(12) United States Patent  (10) Patent No.: US 8,962,606 B2
Hitchcock et al.  (45) Date of Patent: Feb. 24, 2015

(54) SUBSTITUTED BENZOSULPHONAMIDES

(75) Inventors: Marion Hitchcock, Berlin (DE); Ingo Hartung, Berlin (DE); Florian Pühler, Berlin (DE)

(73) Assignee: Bayer Intellectual Property GmbH, Monheim, DE (US)

( * ) Notice: Subject to any disclaimer, the term of this patent is extended or adjusted under 35 U.S.C. 154(b) by 0 days.

(21) Appl. No.: 13/502,548

(22) PCT Filed: Oct. 7, 2010

(86) PCT No.: PCT/EP2010/006124
§ 371 (c)(1),
(2), (4) Date: Jul. 13, 2012

(87) PCT Pub. No.: WO2011/047788
PCT Pub. Date: Apr. 28, 2011

(65) Prior Publication Data
US 2012/0269804 A1 Oct. 25, 2012

(30) Foreign Application Priority Data
Oct. 21, 2009 (EP) ..................... 09075471

(51) Int. Cl.
A61K 31/33 (2006.01)
C07C 311/14 (2006.01)
C07C 307/10 (2006.01)
C07C 311/08 (2006.01)

(52) U.S. Cl.
CPC ............ *C07C 311/14* (2013.01); *C07C 307/10* (2013.01); *C07C 311/08* (2013.01); C07C 2101/02 (2013.01); C07C 2101/04 (2013.01)
USPC ........................................................ 514/183

(58) Field of Classification Search
USPC .......................................................... 514/183
See application file for complete search history.

(56) References Cited

FOREIGN PATENT DOCUMENTS

WO WO 2008/138639 A1 * 11/2008 ............ C07C 217/92

* cited by examiner

*Primary Examiner* — Wu-Cheng Winston Shen
*Assistant Examiner* — Christopher R Stone

(57) ABSTRACT

The present invention relates to substituted benzosulphonamide compounds of general formula (I): in which R1, R2, R3, R4, R5 and A are as defined in the claims, to methods of preparing said compounds, to pharmaceutical compositions and combinations comprising said compounds and to the use of said compounds for manufacturing a pharmaceutical composition for the treatment or prophylaxis of a disease, in particular of a hyper-proliferative and/or angiogenesis disorder, as a sole agent or in combination with other active ingredients.

(I)

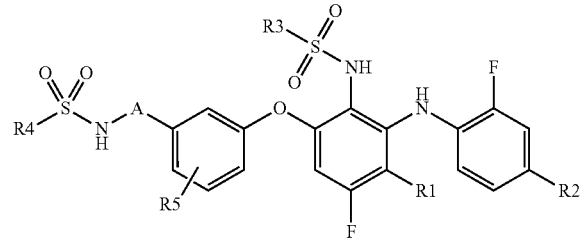

13 Claims, No Drawings

SUBSTITUTED BENZOSULPHONAMIDES

FIELD OF THE INVENTION

The present invention relates to substituted benzosulphonamides, (hereinafter referred to as "compounds of general formula (I)") as described and defined herein, to methods of preparing said compounds, to pharmaceutical compositions and combinations comprising said compounds and to the use of said compounds for manufacturing a pharmaceutical composition for the treatment or prophylaxis of a disease, in particular of a hyper-proliferative and/or angiogenesis disorder, as a sole agent or in combination with other active ingredients.

BACKGROUND OF THE INVENTION

Cancer is a disease resulting from an abnormal growth of tissue. Certain cancers have the potential to invade into local tissues and also metastasize to distant organs. This disease can develop in a wide variety of different organs, tissues, and cell types. Therefore, the term "cancer" refers to a collection of over a thousand different diseases.

Over 4.4 million people worldwide were diagnosed with breast, colon, ovarian, lung, or prostate cancer in 2002 and over 2.5 million people died of these devastating diseases (Globocan 2002 Report). In the United States alone, over 1.25 million new cases and over 500,000 deaths from cancer were predicted in 2005. The majority of these new cases were expected to be cancers of the colon (~100,000), lung (~170,000), breast (~210,000) and prostate (~230,000). Both the incidence and prevalence of cancer is predicted to increase by approximately 15% over the next ten years, reflecting an average growth rate of 1.4% [1].

Accumulating evidence suggests that cancer can be envisioned as a "signaling disease", in which alterations in the cellular genome affecting the expression and/or function of oncogenes and tumor suppressor genes would ultimately affect the transmission of signals that normally regulate cell growth, differentiation, and programmed cell death (apoptosis). Unraveling the signaling pathways that are dysregulated in human cancers has resulted in the design of an increasing number of mechanism-based therapeutic agents [2]. Signal transduction inhibition as a therapeutic strategy for human malignancies has recently met with remarkable success, as exemplified by the development of Gleevec for the treatment of chronic myelogenous leukemia (CML) and gastrointestinal stromal tumors (GIST), heralding a new era of "molecularly-targeted" therapies [3-5].

The mitogen-activated protein kinase (MAPK) module is a key integration point along the signal transduction cascade that links diverse extracellular stimuli to proliferation, differentiation and survival. Scientific studies over the last twenty years have led to a quite detailed molecular dissection of this pathway, which has now grown to include five different MAPK subfamilies [extracellular signal-regulated kinases ERK-1/2, c-Jun-N-terminal kinases (JNKs), p38 kinases, ERK-3/4, and ERK-5], with distinct molecular and functional features [6-8]. While certain subfamilies, such as the p38 family, are becoming therapeutic targets in inflammatory and degenerative diseases, the MAPK cascade that proceeds from Ras to ERK-1/2 (the main mitogenic pathway initiated by peptide growth factors) is starting to emerge as a prime target for the molecular therapy of different types of human cancers [9-11], The MAPK pathway is aberrantly activated in many human tumors as a result of genetic and epigenetic changes, resulting in increased proliferation and resistance to apoptotic stimuli. In particular, mutated oncogenic forms of Ras are found in 50% of colon and >90% of pancreatic cancers [12]. Recently, BRAF mutations have been found in >60% of malignant melanoma [13]. These mutations result in a constitutively activated MAPK pathway. In addition, overexpression of or mutational activation of certain receptor tyrosine kinases can also lead to increased activation of the Raf-MEK-ERK pathway.

The modular nature of the Raf/MEK/ERK cascade becomes less pleiotropic at the crossover point that is regulated by MEK [14]. No substrates for MEK have been identified other than ERK-1/2. Phosphorylated ERK is the product of MEK activity and thus its detection in cancer cells and in tumor tissues provides a direct measure of MEK inhibition. The selectivity of MEK for ERK1/2 coupled with the availability of antibodies specific for the dually phosphorylated and activated form of ERK, makes MEK an attractive target for anticancer drug development. In addition, it was recently shown that MEK activation regulates matrix mineralization (*Blood* 2007, 40, 68), thereby modulation of MEK activity may also be applicable for the treatment of diseases caused by or accompanied with dysregulation of tissue mineralization, more specifically for the treatment of diseases caused by or accompanied with dysregulation of bone mineralization.

First-generation MEK inhibitors, PD98059 [15] and U0126 [16], do not appear to compete with ATP and thus are likely to have distinct binding sites on MEK; these is compounds have been extensively used in model systems in vitro and in vivo to attribute biological activities to ERK1/2. A second-generation MEK1/2 inhibitor, PD184352 (now called CI-1040), has an $IC_{50}$ in the low nanomolar range, enhanced bioavailability, and also appears to work via an allosteric, non ATP-competitive mechanism [17]. Oral treatment with CI-1040 has been shown to inhibit colon cancer growth in vivo in mouse models [18] and this compound was evaluated in phase I/II clinical trials in humans where it eventually failed because of insufficient efficacy [19]. Further allosteric MEK inhibitors have recently entered the clinic but were found to have limitations such as poor exposure profiles, limited efficacy and/or toxicity issues. Small molecules MEK inhibitors have been disclosed, including in U.S. Patent Publications Nos. 2003/0232869, 2004/0116710, 2003/0216420 and in U.S. patent application Ser. Nos. 10/654,580 and 10/929, 295 each of which is hereby incorporated by reference. A number of additional patent applications have appeared in the last few years including U.S. Pat. No. 5,525, 6625; WO 98/43960; WO 99/01421; WO 99/01426; WO 00/41505; WO 00/41994; WO 00/42002; WO 00/42003; WO 00/42022; WO 00/42029; WO 00/68201; WO 01/68619; WO 02/06213; WO 03/077914; WO 03/077855; WO 04/083167; WO 05/0281126; WO 05/051301; WO 05/121142; WO 06/114466; WO 98/37881; WO 00/35435; WO 00/35436; WO 00/40235; WO 00/40237; WO 01/05390; WO 01/05391; WO 01/05392; WO 01/05393; WO 03/062189; WO 03/062191; WO 04/056789; WO 05/000818; WO 05/007616; WO 05/009975; WO 05/051300; WO05/051302; WO 05/028426; WO 06/056427; WO 03/035626; and WO 06/029862.

Despite advancements in the art, there remains a need for cancer treatments and anti-cancer compounds. More specifically, there remains a need for structurally novel MEK inhibitors with a balanced potency-properties profile. It would be especially desirable to identify novel MEK inhibitors which incorporate structural motifs which have not been previously exemplified as being compatible with potent MEK inhibition. It would be especially favorable if these structural motifs would further allow for is improvement of MEK potency and/or modulation of compound properties (including physico-chemical, pharmacodynamical and pharmacokinetical properties).

WO 2008/138639 (Bayer Schering Pharma Aktiengesellschaft) relates to substituted phenylaminobenzene compounds, pharmaceutical compositions containing such compounds and the use of such compounds or compositions for treating hyperproliferative and/or angiogenesis disorders. Said compounds were found to be potent and selective MEK inhibitors. Said compounds are derived from a 1-substituted-2-phenylamino-phenyl scaffold with a further specifically substituted side chain in the 6-position of the phenyl scaffold. This finding was surprising as inspection of published phenyl-scaffold-derived MEK inhibitors and previous structure-activity relationship analysis (see for example Haile Tecle/ Pfizer Global Research: "MEK inhibitors", presented at Drew University, 15 Jun. 2006) suggested that in phenyl-scaffold-based MEK inhibitors larger 6-substituents are detrimental for achieving high MEK inhibitory potency. Said compounds are potent MEK inhibitors and inhibit activation of the MEK-ERK pathway.

However, none of the state of the art described above describes the selected compounds of general formula (I) of the present invention, which bear a selected substituent in 1-position of the central phenyl ring (a selected sulphonamide group of general formula —NHS(O)$_2$R3), and bear a selected substituent in the 3-position of the western phenyl ring (a specially selected sulphonamide group of general formula —NHS(O)$_2$R4), or a stereoisomer, a tautomer, an N-oxide, a hydrate, a solvate, or a salt thereof, or a mixture of same, as described and defined herein, and as hereinafter referred to as "compounds of the present invention", or their pharmacological activity.

It has now been found, and this constitutes the basis of the present invention, that said compounds of the present invention have surprising and advantageous properties.

In particular, said compounds of the present invention have surprisingly been found to effectively strongly inhibit cancer cell proliferation not only in B-Raf mutated human A375 melanoma cells, but also in K-Ras-mutated human A549 non small cell lung cancer cells and in K-Ras mutated human HCT116 colorectal cancer cells. More surprisingly, compounds of the present invention exhibit a stronger cancer cell proliferation inhibition in comparison to that of a compound from prior art document WO 2008/138639.

In view of this, said compounds of general formula (I) of the present invention may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by the mitogen activated protein kinase (MEK-ERK) pathway, such as, for example, haemotological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

DESCRIPTION OF THE INVENTION

In accordance with a first aspect, the present invention covers compounds of general formula (I):

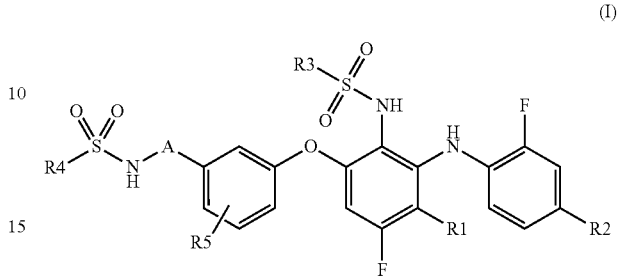

in which:
R1 is a hydrogen atom or a fluorine atom;
R2 is a halogen atom or a C$_2$-alkynyl group;
R3 is an —NH$_2$, —NH(C$_1$-C$_6$-alkyl), —N(C$_1$-C$_6$-alkyl)$_2$, —C$_1$-C$_6$-alkyl, or —C$_3$-C$_6$-cycloalkyl group;
R4 is an —NH$_2$, —NH(C$_1$-C$_6$-alkyl), —N(C$_1$-C$_6$-alkyl)$_2$, —C$_1$-C$_6$-alkyl, or —C$_3$-C$_6$-cycloalkyl group;
R5 is a halogen atom, or a —C$_1$-C$_6$-alkyl or —O—C$_1$-C$_6$-alkyl group;
A is —(CH$_2$)$_n$—, in which n=0, or 1;
or a tautomer, stereoisomer, N-oxide, salt, hydrate, solvate, metabolite, or prodrug thereof.

Definitions

The terms as mentioned in the present text have preferably the following meanings:

The term "halogen atom" or "halo" is to be understood as meaning a fluorine, chlorine, bromine or iodine atom.

The term "C$_1$-C$_{10}$-alkyl" is to be understood as preferably meaning a linear or branched, saturated, monovalent hydrocarbon group having 1, 2, 3, 4, 5, 6, 7, 8, 9 or 10 carbon atoms, particularly 1, 2, 3, 4, 5 or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2 or 3 carbon atoms ("C$_1$-C$_3$-alkyl"), methyl, ethyl, n-propyl- or iso-propyl.

The term "halo-C$_1$-C$_{10}$-alkyl" is to be understood as preferably meaning a linear or branched, saturated, monovalent hydrocarbon group in which the term "C$_1$-C$_{10}$-alkyl" is defined supra, and in which one or more hydrogen atoms is replaced by a halogen atom, in identically or differently, i.e. one halogen atom being independent from another. Particularly, said halogen atom is F. Said halo-C$_1$-C$_{10}$-alkyl group is, for example, —CF$_3$, —CHF$_2$, —CH$_2$F, —CF$_2$CF$_3$, or —CH$_2$CF$_3$.

The term "C$_1$-C$_{10}$-alkoxy" is to be understood as preferably meaning a linear or branched, saturated, monovalent, hydrocarbon group of formula —O-alkyl, in which the term "alkyl" is defined supra, e.g. a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof.

The term "halo-C$_1$-C$_{10}$-alkoxy" is to be understood as preferably meaning a linear or branched, saturated, monovalent C$_1$-C$_{10}$-alkoxy group, as defined supra, in which one or more of the hydrogen atoms is replaced, in identically or differently, by a halogen atom. Particularly, said halogen atom is F. Said halo-$C_1$-$C_{10}$alkoxy group is, for example, —$OCF_3$, —$OCHF_2$, —$OCH_2F$, —$OCF_2CF_3$, or —$OCH_2CF_3$.

The term "$C_1$-$C_{10}$-alkoxy-$C_1$-$C_{10}$-alkyl" is to be understood as preferably meaning a linear or branched, saturated, monovalent alkyl group, as defined supra, in which one or more of the hydrogen atoms is replaced, in identically or differently, by a $C_1$-$C_{10}$-alkoxy group, as defined supra, e.g. methoxyalkyl, ethoxyalkyl, propyloxyalkyl, iso-propoxyalkyl, butoxyalkyl, iso-butoxyalkyl, tert-butoxyalkyl, sec-butoxyalkyl, pentyloxyalkyl, iso-pentyloxyalkyl, hexyloxyalkyl group, in which the term "$C_1$-$C_{10}$ alkyl" is defined supra, or an isomer thereof.

The term "halo-$C_1$-$C_{10}$-alkoxy-$C_1$-$C_{10}$-alkyl" is to be understood as preferably meaning a linear or branched, saturated, monovalent $C_1$-$C_{10}$-alkoxy-$C_1$-$C_{10}$-alkyl group, as defined supra, in which one or more of the hydrogen atoms is replaced, in identically or differently, by a halogen atom. Particularly, said halogen atom is F. Said halo-$C_1$-$C_{10}$-alkoxy-$C_1$-$C_{10}$-alkyl group is, for example, —$CH_2CH_2OCF_3$, —$CH_2CH_2OCHF_2$, —$CH_2CH_2OCH_2F$, —$CH_2CH_2OCF_2CF_3$, or —$CH_2CH_2OCH_2CF_3$.

The term "$C_2$-$C_{10}$-alkenyl" is to be understood as preferably meaning a linear or branched, monovalent hydrocarbon group, which contains one or more double bonds, and which has 2, 3, 4, 5, 6, 7, 8, 9 or 10 carbon atoms, particularly 2 or 3 carbon atoms ("$C_2$-$C_3$-alkenyl"), it being understood that in the case in which said alkenyl group contains more than one double bond, then said double bonds may be isolated from, or conjugated with, each other. Said alkenyl group is, for example, a vinyl, allyl, (E)-2-methylvinyl, (Z)-2-methylvinyl, homoallyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, isopropenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (Z)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl, (Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-enyl, (Z)-1-ethylbut-1-enyl, 2-propylprop-2-enyl, 1-propylprop-2-enyl, 2-isopropylprop-2-enyl, 1-isopropylprop-2-enyl, (E)-2-propylprop-1-enyl, (Z)-2-propylprop-1-enyl, (E)-1-propylprop-1-enyl, (Z)-1-propylprop-1-enyl, (E)-2-isopropylprop-1-enyl, (Z)-2-isopropylprop-1-enyl, (E)-1-isopropylprop-1-enyl, (Z)-1-isopropylprop-1-enyl, (E)-3,3-dimethylprop-1-enyl, (Z)-3,3-dimethylprop-1-enyl, 1-(1,1-dimethylethyl)ethenyl, buta-1,3-dienyl, penta-1,4-dienyl, hexa-1,5-dienyl, or methylhexadienyl group. Particularly, said group is vinyl or allyl.

The term "$C_2$-$C_{10}$-alkynyl" is to be understood as preferably meaning a linear or branched, monovalent hydrocarbon group which contains one or more triple bonds, and which contains 2, 3, 4, 5, 6, 7, 8, 9 or 10 carbon atoms, particularly 2 or 3 carbon atoms ("$C_2$-$C_3$-alkynyl"). Said $C_2$-$C_{10}$-alkynyl group is, for example, ethynyl, prop-1-ynyl, prop-2-ynyl, but-1-ynyl, but-2-ynyl, but-3-ynyl, pent-1-ynyl, pent-2-ynyl, pent-3-ynyl, pent-4-ynyl, hex-1-ynyl, hex-2-inyl, hex-3-inyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-inyl, 1,1-dimethylbut-3-ynyl, 1,1-dimethylbut-2-ynyl, or 3,3-dimethylbut-1-ynyl group. Particularly, said alkynyl group is ethynyl, prop-1-ynyl, or prop-2-inyl.

The term "$C_3$-$C_{10}$-cycloalkyl" is to be understood as preferably meaning a saturated, monovalent, mono-, or bicyclic hydrocarbon ring which contains 3, 4, 5, 6, 7, 8, 9, or carbon atoms, particularly 3, 4, 5, or 6 carbon atoms ("$C_3$-$C_6$-cycloalkyl"). Said $C_3$-$C_{10}$-cycloalkyl group is for example, a monocyclic hydrocarbon ring, e.g. a cyclopropyl, cyclobutyl, cyclopentyl, cyclohexyl, cycloheptyl, cyclooctyl, cyclononyl or cyclodecyl group, or a bicyclic hydrocarbon ring, e.g. a perhydropentalenylene or decalin ring. Said cycloalkyl ring can optionally contain one or more double bonds e.g. cycloalkenyl, such as a cyclopropenyl, cyclobutenyl, cyclopentenyl, cyclohexenyl, cycloheptenyl, cyclooctenyl, cyclononenyl, or cyclodecenyl group, wherein the bond between said ring with the rest of the molecule may be to any carbon atom of said ring, be it saturated or unsaturated.

The term "alkylene" is understood as preferably meaning an optionally substituted hydrocarbon chain (or "tether") having 1, 2, 3, 4, 5, or 6 carbon atoms, i.e. an optionally substituted —$CH_2$— ("methylene" or "single membered tether" or, for example —$C(Me)_2$-), —$CH_2$—$CH_2$— ("ethylene", "dimethylene", or "two-membered tether"), —$CH_2$—$CH_2$—$CH_2$— ("propylene", "trimethylene", or "three-membered tether"), —$CH_2$—$CH_2$—$CH_2$—$CH_2$— ("butylene", "tetramethylene", or "four-membered tether"), —$CH_2$—$CH_2$—$CH_2$—$CH_2$—$CH_2$— ("pentylene", "pentamethylene" or "five-membered ether"), or —$CH_2$—$CH_2$—$CH_2$—$CH_2$—$CH_2$—$CH_2$— ("hexylene", "hexamethylene", or six-membered tether") group. Particularly, said alkylene tether has 1, 2, 3, 4, or 5 carbon atoms, more particularly 1 or 2 carbon atoms.

The term "$C_1$-$C_6$", as used throughout this text, e.g. in the context of the definition of "$C_1$-$C_6$-alkyl", "$C_1$-$C_6$-haloalkyl", "$C_1$-$C_6$-alkoxy", or "$C_1$-$C_6$-haloalkoxy" is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$; $C_3$-$C_4$, $C_1$-$C_2$, $C_1$-$C_3$, $C_1$-$C_4$, $C_1$-$C_5$, $C_1$-$C_6$; particularly $C_1$-$C_2$, $C_1$-$C_3$, $C_1$-$C_4$, $C_1$-$C_5$, $C_1$-$C_6$; more particularly $C_1$-$C_4$, in the case of "$C_1$-$C_6$-haloalkyl" or "$C_1$-$C_6$-haloalkoxy" even more particularly $C_1$-$C_2$.

Similarly, as used herein, the term "$C_2$-$C_6$", as used throughout this text, e.g. in the context of the definitions of "$C_2$-$C_6$-alkenyl" and "$C_2$-$C_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_3$-$C_5$, $C_3$-$C_4$, $C_2$-$C_3$, $C_2$-$C_4$, $C_2$-$C_5$; particularly $C_2$-$C_3$.

Further, as used herein, the term "$C_3$-$C_{10}$", as used throughout this text, e.g. in the context of the definition of "$C_3$-$C_{10}$-cycloalkyl", is to be understood as meaning a cycloalkyl group having a finite number of carbon atoms of 3 to 10, i.e. 3, 4, 5, 6, 7, 8, 9 or 10 carbon atoms, particularly 3, 4, 5 or 6 carbon atoms. It is to be understood further that said term "$C_3$-$C_{10}$" is to be interpreted as any sub-range comprised therein, e.g. $C_3$-$C_{10}$, $C_4$-$C_9$, $C_5$-$C_8$, $C_6$-$C_7$; particularly $C_3$-$C_6$.

As used herein, the term "one or more times", e.g. in the definition of the substituents of the compounds of the general formulae of the present invention, is understood as meaning "one, two, three, four or five times, particularly one, two, three or four times, more particularly one, two or three times, even more particularly one or two times".

Where the plural form of the word compounds, salts, polymorphs, hydrates, solvates and the like, is used herein, this is taken to mean also a single compound, salt, polymorph, isomer, hydrate, solvate or the like.

The compounds of this invention may contain one or more asymmetric centre, depending upon the location and nature of the various substituents desired. Asymmetric carbon atoms may be present in the (R) or (S) configuration, resulting in racemic mixtures in the case of a single asymmetric centre, and diastereomeric mixtures in the case of multiple asymmetric centres. In certain instances, asymmetry may also be present due to restricted rotation about a given bond, for example, the central bond adjoining two substituted aromatic rings of the specified compounds.

Substituents on a ring may also be present in either cis or trans form. It is intended that all such configurations (including enantiomers and diastereomers), are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Diacel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, viz.:

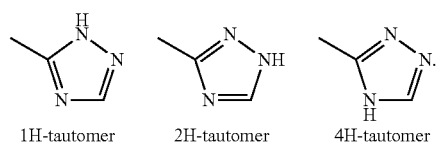

1H-tautomer     2H-tautomer     4H-tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol. Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

As used herein, the term "in vivo hydrolysable ester" is understood as meaning an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, and may be formed at any carboxy group in the compounds of this invention.

An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Furthermore, the present invention includes all possible crystalline forms, or polymorphs, of the compounds of the present invention, either as single polymorphs, or as a mixture of more than one polymorphs, in any ratio.

In accordance with a second aspect, the present invention covers compounds of general formula (I), supra, in which:
R1 is a hydrogen atom or a fluorine atom;
R2 is a fluorine atom or a $C_2$-alkynyl group;
R3 is an —$NH_2$, —$NH(C_1$-$C_6$-alkyl), —$N(C_1$-$C_6$-alkyl)$_2$, —$C_1$-$C_6$-alkyl, or —$C_3$-$C_6$-cycloalkyl group;
R4 is an —$NH_2$, —$NH(C_1$-$C_6$-alkyl), —$N(C_1$-$C_6$-alkyl)$_2$, —$C_1$-$C_6$-alkyl, or —$C_3$-$C_6$-cycloalkyl group;
R5 is a fluorine atom or a methyl group;
A is —$(CH_2)_n$—, in which n=0, or 1;
or a tautomer, stereoisomer, N-oxide, salt, hydrate, solvate, metabolite, or prodrug thereof.

In accordance with a third aspect, the present invention covers compounds of general formula (I), supra, in which:
R1 is a hydrogen atom or a fluorine atom;
R2 is a fluorine atom or a $C_2$-alkynyl group;
R3 is an —$NH_2$, —$NH(C_1$-$C_6$-alkyl), —$N(C_1$-$C_6$-alkyl)$_2$, —$C_1$-$C_6$-alkyl, or —$C_3$-$C_6$-cycloalkyl group;
R4 is an —$NH_2$, methyl, ethyl, n-propyl, iso-propyl or cyclopropyl or cyclobutyl group;
R5 is a fluorine atom or a methyl group;
A is —$(CH_2)_n$—, in which n=0, or 1;
or a tautomer, stereoisomer, N-oxide, salt, hydrate, solvate, metabolite, or prodrug thereof.

In accordance with a fourth aspect, the present invention covers compounds of general formula (I), supra, in which:
R1 is a hydrogen atom or a fluorine atom;
R2 is a fluorine atom or a $C_2$-alkynyl group;
R3 is an —$NH_2$, methyl, ethyl, n-propyl, iso-propyl, cyclopropyl or cyclobutyl group;
R4 is an —$NH_2$, methyl, ethyl, n-propyl, iso-propyl, cyclopropyl or cyclobutyl group;
R5 is a fluorine atom or a methyl group;
A is —$(CH_2)_n$—, in which n=0, or 1;
or a tautomer, stereoisomer, N-oxide, salt, hydrate, solvate, metabolite, or prodrug thereof.

In a further embodiment of the above-mentioned aspects, the invention relates to compounds of formula (I), wherein $R^1$ is a hydrogen atom or a fluorine atom.

In a further embodiment of the above-mentioned aspects, the invention relates to compounds of formula (I), wherein R2 is a halogen atom or a $C_2$-alkynyl group.

In a further embodiment of the above-mentioned aspects, the invention relates to compounds of formula (I), wherein R3 is an —$NH_2$, —$NH(C_1$-$C_6$-alkyl), —$N(C_1$-$C_6$-alkyl)$_2$, —$C_1$-$C_6$-alkyl, or —$C_3$-$C_6$-cycloalkyl group.

In a further embodiment of the above-mentioned aspects, the invention relates to compounds of formula (I), wherein R4 is an —$NH_2$, —$NH(C_1$-$C_6$-alkyl), —$N(C_1$-$C_6$-alkyl)$_2$, —$C_1$-$C_6$-alkyl, or —$C_3$-$C_6$-cycloalkyl group.

In a further embodiment of the above-mentioned aspects, the invention relates to compounds of formula (I), wherein R5 is a halogen atom, or a —$C_1$-$C_6$-alkyl or —O—$C_1$-$C_6$-alkyl group.

In a further embodiment of the above-mentioned aspects, the invention relates to compounds of formula (I), wherein A is —$(CH_2)_n$—, in which n=0.

In a further embodiment of the above-mentioned aspects, the invention relates to compounds of formula (I), wherein A is —$(CH_2)_n$—, in which n=1.

In a further embodiment of the above-mentioned aspects, the invention relates to compounds of formula (I), wherein R5 is a fluorine atom or a methyl group.

In a further embodiment of the above-mentioned aspects, the invention relates to compounds of formula (I), wherein R4 is an —$NH_2$, methyl, ethyl, n-propyl, iso-propyl, cyclopropyl or cyclobutyl group.

In a further embodiment of the above-mentioned aspects, the invention relates to compounds of formula (I), wherein R3 is an —$NH_2$, methyl, ethyl, n-propyl, iso-propyl, cyclopropyl or cyclobutyl group.

It is to be understood that the present invention relates to any sub-combination within any embodiment of the present invention of compounds of general formula (I), supra.

In a further aspect, the present invention covers compounds of general formula (I) which are disclosed in the Example section of this text, infra.

In accordance with another aspect, the present invention covers a method of preparing compounds of the present invention, the method comprising the steps as described herein.

In accordance with a further aspect, the present invention covers intermediate compounds which are useful in the preparation of compounds of the present invention of general formula (I), particularly in the method described herein. In particular, the present invention covers compounds of general formula (4):

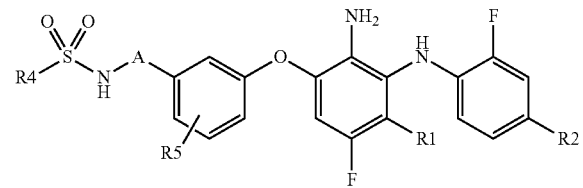

(4)

in which R1, R2, R4, R5 and A are as defined supra as for general formula (I), and compounds of general formula (8):

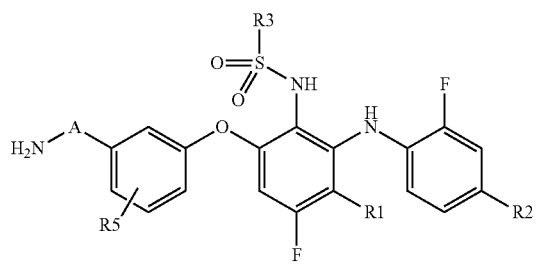

(8)

in which R1, R2, R3, R5 and A are as defined supra as for general formula (I), and compounds of general formula (12):

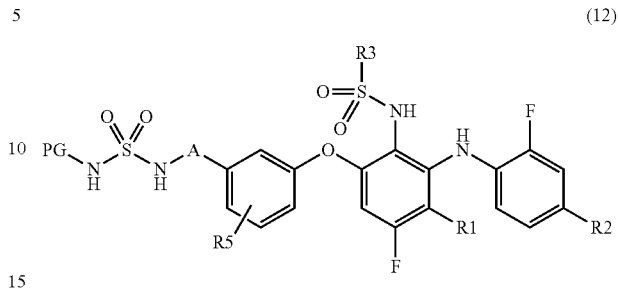

(12)

in which R1, R2, R3, R5 and A are as defined supra for general formula (I), and PG represents an acid-labile protecting group.

In accordance with a further aspect, the present invention relates to the use of the intermediate compound of general formula (4), supra, or of the intermediate compound of general formula (8), supra, or of the intermediate compound of general formula (12), supra, for the preparation of a compound of general formula (I), supra.

Experimental Details and General Processes
Abbreviations and Acronyms

A comprehensive list of the abbreviations used by organic chemists of ordinary skill in the art appears in The ACS Style Guide (third edition) or the Guidelines for Authors for the *Journal of Organic Chemistry*. The abbreviations contained in said lists, and all abbreviations utilized by organic chemists of ordinary skill in the art are hereby incorporated by reference. For purposes of this invention, the chemical elements are identified in accordance with the Periodic Table of the Elements, CAS version, Handbook of Chemistry and Physics, 67th Ed., 1986-87.

More specifically, when the following abbreviations are used throughout this disclosure, they have the following meanings:

$Ac_2O$ acetic anhydride
ACN acetonitrile
AcO (or OAc) acetate
anhyd anhydrous
aq aqueous
Ar aryl
atm atmosphere
ATP adenosine triphosphate
b.i.d. twice a day
Biotage silica gel chromatographic system, Biotage Inc.
Bn benzyl
bp boiling point
Bz benzoyl
BOC tert-butoxycarbonyl
n-BuOH n-butanol
t-BuOH tert-butanol
t-BuOK potassium tert-butoxide
calcd calculated
CDI carbonyl diimidazole
$CD_3OD$ methanol-$d_4$
Celite® diatomaceous earth filter agent, Celite Corp.
CI-MS chemical ionization mass spectroscopy
$^{13}C$ NMR carbon-13 nuclear magnetic resonance
conc concentrated
DCC dicyclohexylcarbodiimide
DCE dichloroethane
DCM dichloromethane dec decomposition
DIBAL diisobutylaluminum hydroxide
DMAP 4-(N,N-dimethylamino)pyidine
DME 1,2-dimethoxyethane
DMF N,N-dimethylformamide
DMSO dimethylsulfoxide
DTT dithiothreitol
E entgegen (configuration)
e.g. for example
EO electron impact
ELSD evaporative light scattering detector
eq equivalent
ERK extracellular signal-regulated kinase
ESI electrospray ionisation
ES-MS electrospray mass spectroscopy
et al. and others
EtOAc ethyl acetate
EtOH ethanol (100%)
EtSH ethanethiol
Et$_2$O diethyl ether
Et$_3$N triethylamine
GC gas chromatography
GC-MS gas chromatography-mass spectroscopy
h hour, hours
$^1$H NMR proton nuclear magnetic resonance
HCl hydrochloric acid
HEPES 4-(2-hydroxyethyl)-1-piperazineethanesulfonic acid
Hex hexane
HMPA hexamethylphosphoramide
HMPT hexamethylphosphoric triamide
HPLC high performance liquid chromatography
IC$_{50}$ drug concentration required for 50% inhibition
i.e. that is
insol insoluble
IPA isopropylamine
IR infrared
J coupling constant (NMR spectroscopy)
LAH lithium aluminum hydride
LC liquid chromatography
LC-MS liquid chromatography-mass spectrometry
LDA lithium diisopropylamide
MAPK mitogen-activated protein kinase
MeCN acetonitrile
MEK MAPK/ERK kinase
MHz megahertz
min minute, minutes
μL microliter
mL milliliter
μM micromolar
mp melting point
MS mass spectrum, mass spectrometry
Ms methanesulfonyl
m/z mass-to-charge ratio
NBS N-bromosuccinimide
nM nanomolar
NMM 4-methylmorpholine
obsd observed
p page
PBS phosphate buffered saline
pp pages
PdCl$_2$dppf [1,1'-bis(diphenylphosphino)ferrocene]dichloropalladium(II)
Pd(OAc)$_2$ palladium acetate
pH negative logarithm of hydrogen ion concentration
pK negative logarithm of equilibrium constant
pK$_a$ negative logarithm of equilibrium constant for association PS-DIEA polystyrene-bound diisopropylethylamine
q quartet (nmr)
qt quintet (nmr)
R$_f$ retention factor (TLC)
RT retention time (HPLC)
rt room temperature
TBAF tetra-n-butylammonium fluoride
TBST tris buffered saline with tween
TEA triethylamine
THF tetrahydrofuran
TFA trifluoroacetic acid
TFFH fluoro-N,N,N',N'-tetramethylformamidinium hexafluorophosphate
TLC thin layer chromatography
TMAD N,N,N',N'-tetramethylethylenediamine
TMSCl trimethylsilyl chloride
Ts p-toluenesulfonyl
v/v volume per volume
w/v weight per volume
w/w weight per weight
Z zusammen (configuration)

General Procedures

In the subsequent paragraphs detailed general procedures for the synthesis of key intermediates and compounds of the present invention are described.

The schemes and procedures described below illustrate general synthetic routes to the compounds of general formula (I) of the invention and are not intended to be limiting. It is obvious to the person skilled in the art that the order of transformations as exemplified in the Schemes can be modified in various ways. The order of transformations exemplified in the Schemes is therefore not intended to be limiting. In addition, interconversion of any of the substituents, R1, R2, R3, R4 or R5 can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, 3$^{rd}$ edition, Wiley 1999). Specific examples are described in the subsequent paragraphs.

A general route for the preparation of compounds of general formula (I) is described in Scheme 1.

Scheme 1

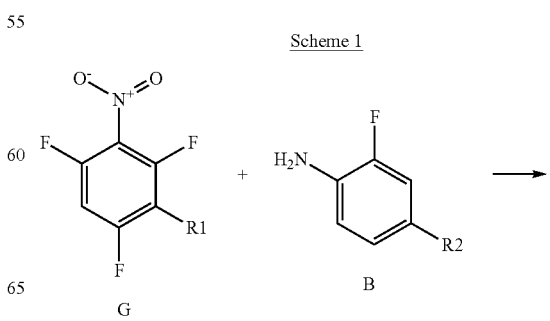

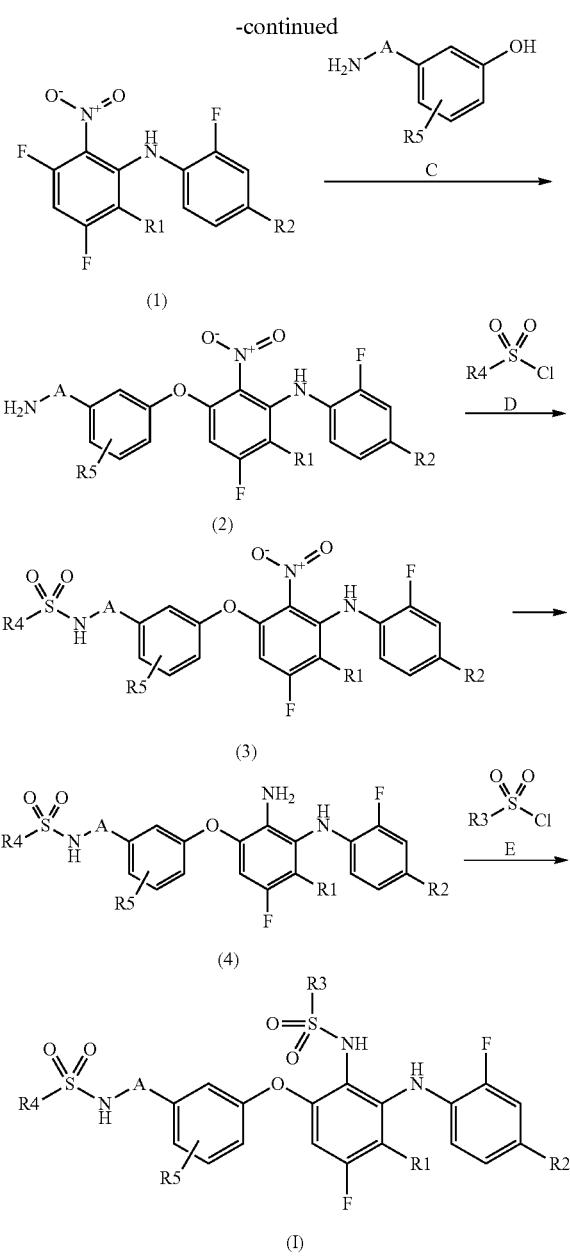

(1)

(2)

(3)

(4)

(I)

Scheme 1 General route for the preparation of compounds of general formula (I), wherein $R^1$, $R^2$, $R^3$, $R^4$, $R^5$ and A have the meaning as given for general formula (I), supra. Compounds G, B, C, D and E are commercially available.

A suitably substituted 1,3,5-trifluoro-2-nitrobenzene of general formula (G) is reacted with a suitably substituted 2-fluoro-aniline of general formula (B), in a suitable solvent system, such as, for example, THF, in the presence of a suitable base, such as, for example, lithium hexamethyldisilazan at temperatures ranging from −78° C. to room temperature, preferably room temperature, to furnish 3,5-difluoro-N-(2-fluorophenyl)-2-nitroaniline intermediates of general formula (1).

Intermediates of general formula (1) are then converted to intermediates of general formula (2) by reaction with a suitably substituted phenol of general formula (C), for example 3-amino phenol, in a suitable solvent system, such as, for example, DMF, in the presence of a suitable base, such as, for example potassium carbonate, at a temperature between room temperature and the boiling point of the respective solvent.

Intermediates of general formula (2) are reacted with a suitable sulfonyl chloride of the general formula (D), for example ethyl sulfonyl chloride, in the presence of a suitable base, such as, for example pyridine, which optionally may function also as solvent, optionally in a suitable solvent such as, for example, dichloromethane, at temperatures ranging from 0° C. to room temperature, to furnish intermediates of general formula (3).

Intermediates of general formula (3) are then converted to intermediates of general formula (4) by reaction with a suitable reducing agent agent, such as, for example, sodium dithionite, in a suitable solvent, such as, for example a THF/water mixture, at temperatures ranging from room temperature to the boiling point of the solvent. Alternative reagents and conditions for reducing nitro groups are known in the art.

Intermediates of general formula (4) are then converted to compounds of general formula (I) by reaction with a suitable sulfonyl chloride of the general formula (E), for example cyclopropane sulfonyl chloride, in the presence of a suitable base, such as, for example, pyridine, which optionally may function also as solvent, optionally in a suitable solvent, such as, for example, dichloromethane, at temperatures ranging from 0° C. to room temperature.

Alternatively, compounds of general formula (I) can be synthesised according to the procedure depicted in Scheme 2. Compounds D, E and H are commercially available or are prepared as described in the specific experimental descriptions below.

Scheme 2

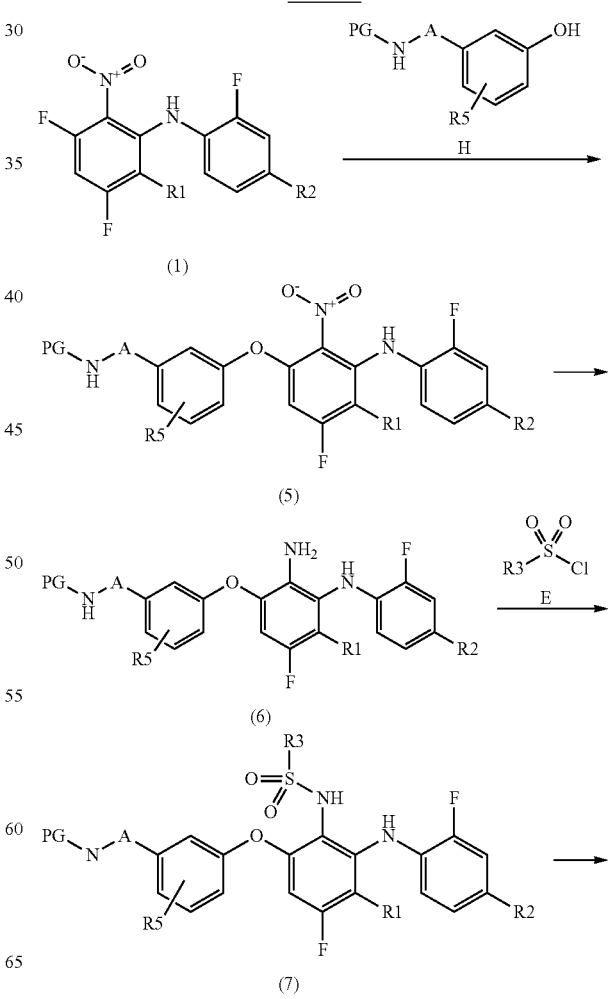

(1)

(5)

(6)

(7)

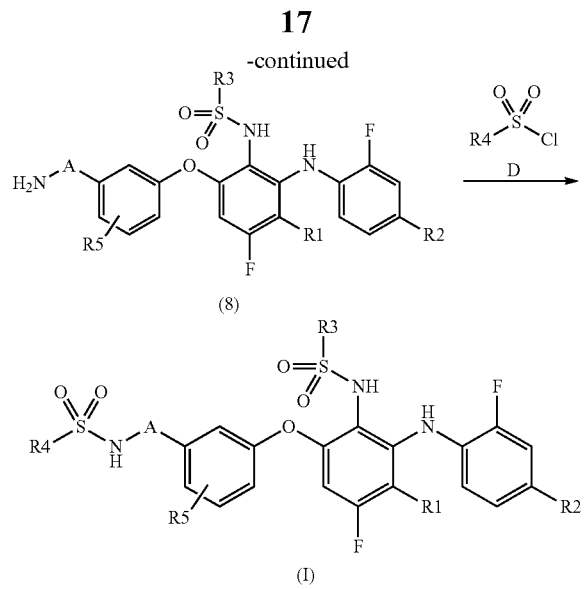

Scheme 2. Alternative general route for the preparation of compounds of general formula (I), wherein $R^1$, $R^2$, $R^3$, $R^4$, $R^5$ and A have the meaning as given for general formula (I), supra. PG represents a "suitable protection group", for example, a tert-butoxy carbonyl (Boc).

Intermediates of general formula (1) are converted to intermediates of general formula (5) by reaction with a suitably protected substituted phenol of general formula (H), for example tert-butyl(3-hydroxyphenyl)carbamate, in a suitable solvent system, such as, for example, DMF, in the presence of a suitable base, such as, for example caesium carbonate, at a temperature between room temperature and the boiling point of the respective solvent.

Intermediates of general formula (5) are then converted to intermediates of general formula (6) by reaction with a suitable reducing agent, such as, for example sodium dithionite, in a suitable solvent, such as, for example THF, at temperatures ranging from room temperature to the boiling point of the solvent.

Intermediates of general formula (6) are then converted to intermediates of general formula (7) by reaction with a suitable sulfonyl chloride of the general formula (E), for example cyclopropane sulfonyl chloride, in the presence of a suitable base, such as, for example, pyridine, in a suitable solvent, such as, for example, pyridine, at temperatures ranging from 0° C. to room temperature.

Intermediates of general formula (7) are converted to intermediates of general formula (8) by cleavage of the protecting group by means known to the person skilled in the art, for example, cleavage of the tert-butoxycarbonyl (Boc) group in the presence of a suitable acid, such as, for example, TFA, in a suitable solvent, such as, for example, DCM, at temperatures ranging from room temperature to the boiling point of the solvent.

Intermediates of general formula (8) are then reacted with a suitable sulfonyl chloride of the general formula (D), for example, isopropyl sulfonyl chloride, in the presence of a suitable base, such as, for example, pyridine, in a suitable solvent, such as, for example, pyridine, at temperatures ranging from 0° C. to room temperature, to furnish compounds of general formula (I).

Alternatively, compounds of general formula (Ic) can be synthesised according to the procedure depicted in Scheme 3. Compounds E and J are commercially available.

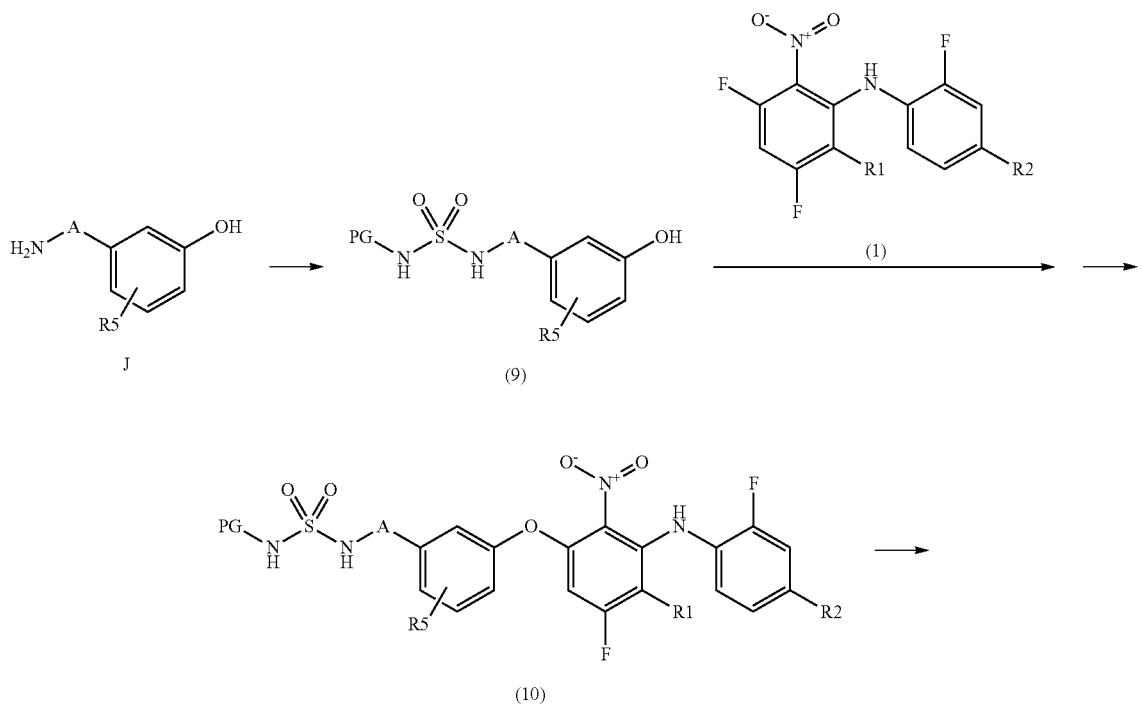

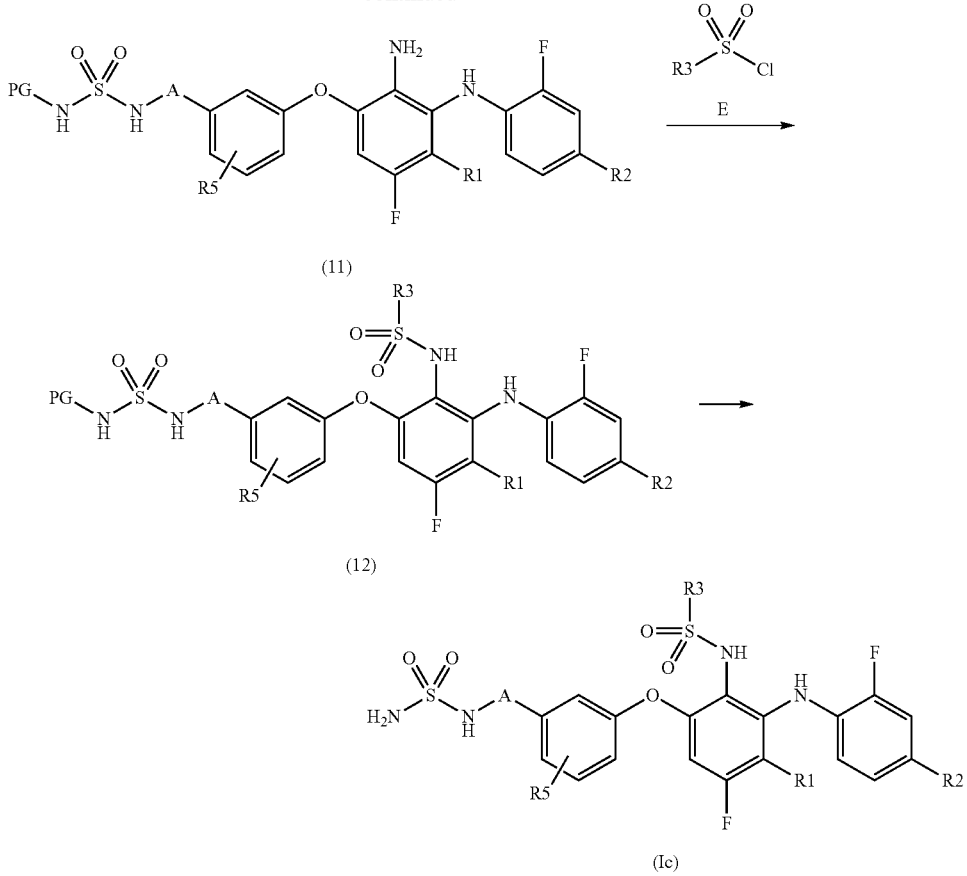

Scheme 3. General route for the preparation of compounds of general formula (Ic), wherein $R^1$, $R^2$, $R^3$, $R^5$ and A have the meaning as given for general formula (I), supra; PG represents a "suitable protection group" for example a tert-butoxy carbonyl (Boc) group.

A suitably substituted phenol of general formula (J), is converted to the corresponding tert-butyloxy carbonyl (BOC) protected sulfamoyl derivative of general formula (9) by reaction with chlorosulfonyl isocyanate and tert. butanol in the presence of a suitable base, such as, for example, triethylamine, at temperatures ranging from 0° C. to room temperature, preferably room temperature [see for example Tetrahedron 1993, 49, 65-76].

Intermediates of general formula (9) are converted to intermediates of general formula (10) by reaction with intermediates of general formula (1), in a suitable solvent system, such as, for example, DMF, in the presence of a suitable base, such as, for example caesium carbonate, at a temperature between room temperature and the boiling point of the respective solvent.

Intermediates of general formula (10) are then converted to intermediates of general formula (11) by reaction with a suitable reduction agent, such as, for example, sodium dithionite, in a suitable solvent, such as, for example, THF, at temperatures ranging from room temperature to the boiling point of the solvent.

Intermediates of general formula (11) are then converted to intermediates of general formula (12) by reaction with a suitable sulfonyl chloride of the general formula (E), for example, cyclopropane sulfonyl chloride, in the presence of a suitable base, such as, for example, pyridine, in a suitable solvent, such as, for example, pyridine, at temperatures ranging from 0° C. to room temperature.

Intermediates of general formula (12) are converted to compounds of general formula (Ic) by cleavage of the protecting group by means known to the person skilled in the art, for example, cleavage of the tert-butoxy carbonyl (Boc) group in the presence of a suitable acid, such as, for example, TFA, in a suitable solvent, such as, for example DCM, at temperatures ranging from room temperature to the boiling point of the solvent.

Compounds of general formula (Ia) can be converted into compounds of general formula (Ib) according to the procedure depicted in Scheme 4.

Scheme 4

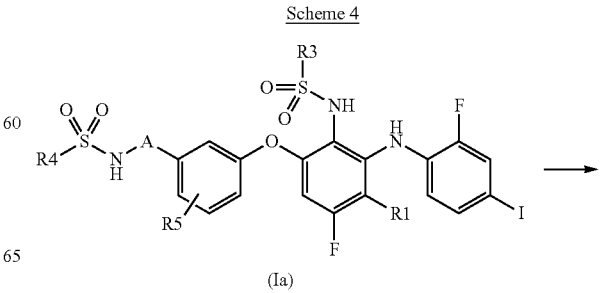

(Ia)

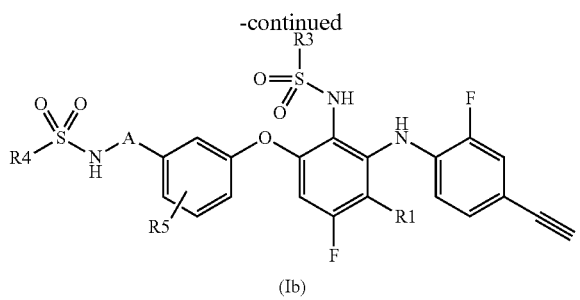

(Ib)

Scheme 4. General process for the transformation of compounds of general formula (Ia) into compounds of general formula (Ib), wherein $R^1$, $R^3$, $R^4$, $R^5$ and A have the meaning as given for general formula (I), supra.

Compounds of general formula (Ia) are converted to compounds of general formula (Ib) by coupling reactions know to the person skilled in the art, preferably by a Sonogashira or Sonogashira-type coupling reaction with acetylene or an acetylene equivalent (vide infra).

An iodo- or bromo-containing intermediate, for example of general formula (Ia), can be reacted with acetylene in the presence of catalytic amounts of a Pd catalyst such as, for example, $PdCl_2(PPh_3)_2$, catalytic amounts of copper iodide, in the presence of a solvent such as DMF and optionally in the presence of a base, such as, for example, a trialkyl amine base, to form the corresponding alkyne derivative (Ib). Alternatively, mono-trialkylsilyl-protected acetylene such as for example, trimethylsilyl (TMS) acetylene, may be employed in such a Sonogashira-type coupling under conditions as described above followed by cleavage of the trialkylsilyl group by treatment with, for example, tetrabutylammonium fluoride or potassium carbonate in methanol. Alternatively, by using tetrabutylammonium fluoride as base in the Sonogashira-type coupling, coupling of TMS acetylene and cleavage of the TMS-group can be achieved in a one pot transformation. Transition metal-catalyzed couplings of (hetero)aryl halides with alkynes and trialkylsilyl alkynes are well known to the person skilled in the art (see for example (a) Chinchilla, R.; Najera, C. Chem. Rev. 2007, 107, 874; (b) Negishi, E.-i., Anastasia, L. Chem. Rev. 2003, 103, 1979; see also: (c) Eur. J. Org. Chem. 2005, 20, 4256; (d) J. Org. Chem. 2006, 71, 2535 and references therein; (e) Chem. Commun. 2004, 17, 1934). Various palladium-catalyst/co-catalyst/ligand/base/solvent combinations have been published in the scientific literature which allow a fine-tuning of the required reaction conditions in order to allow for a broad set of additional functional groups on both coupling partners (see references in the above cited reviews). Additionally, recently developed procedures employing e.g. zinc acetylides, alkynyl magnesium salts or alkynyl trifluoroborate salts further broaden the scope of this process.

Specific Experimental Descriptions

NMR peak forms in the following specific experimental descriptions are stated as they appear in the spectra, possible higher order effects have not been considered. Names of compounds were generated using ACD/Name Batch version 12.00. In some cases generally accepted names of commercially available reagents were used. Reactions employing microwave irradiation may be run with a Biotage Initator® microwave oven optionally equipped with a robotic unit. The reported reaction times employing microwave heating are intended to be understood as fixed reaction times after reaching the indicated reaction temperature. The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. from Separtis such as Isolute® Flash silica gel or Isolute® Flash $NH_2$ silica gel in combination with a Flashmaster II autopurifier (Argonaut/Biotage) and eluents such as gradients of hexane/ethyl acetate or DCM/ethanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid or aqueous ammonia. In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc) of a compound of the present invention as isolated as described herein is not necessarily the only form in which said compound can be applied to a biological assay in order to quantify the specific biological activity.

The percentage yields reported in the following examples are based on the starting component that was used in the lowest molar amount. Air and moisture sensitive liquids and solutions were transferred via syringe or cannula, and introduced into reaction vessels through rubber septa. Commercial grade reagents and solvents were used without further purification. The term "concentrated under reduced pressure" refers to use of a Buchi rotary evaporator at a minimum pressure of approximately 15 mm of Hg. All temperatures are reported uncorrected in degrees Celsius (° C.).

In order that this invention may be better understood, the following examples are set forth. These examples are for the purpose of illustration only, and are not to be to construed as limiting the scope of the invention in any manner. All publications mentioned herein are incorporated by reference in their entirety.

In the subsequent paragraphs detailed general procedures for the synthesis of key intermediates and compounds of the present invention are described.

General Procedure 1 (GP 1): Sulfonamide formation 1. eq. of the respective amine were dissolved in pyridine (ca. 4 mL per mmol amine) and treated with 1.2 to 2 eq. of the respective sulfonyl chloride. The reaction mixture was stirred at rt until LCMS analysis showed complete starting material consumption. Optionally, additional aliquots of the respective sulfonyl chloride were added to complete the turnover. The reaction mixture was quenched with water and extracted several times with dichloromethane. The combined organic layers were washed with brine, filtered and concentrated in vacuo to give the crude target compound. Preparative HPLC purification or flash column chromatography provided the respective target compound.

Analytical LCMS Conditions A:

LCMS-data given in the subsequent specific experimental descriptions refer (unless otherwise noted) to the following conditions:

| | |
|---|---|
| System: | Waters Aqcuity UPLC-MS: Binary Solvent Manager, Sample Manager/Organizer, PDA, ELSD, ZQ4000 |
| Column: | Aqcuity UPLC BEH C18 1.7 50 x 2.1 mm |
| Solvent: | A = H2O + 0.05% HCOOH<br>B = Acetonitril + 0.05% HCOOH |
| Gradient: | 0-1.6 min 1-99% B, 1.6-2.0 min 99% B |
| Flow: | 0.8 mL/min |
| Temperature: | 60° C. |
| Injection: | 2.0 µl |
| Detection: | DAD scan range 210-400 nm -> Peaktable<br>ELSD -> Peaktable<br>MS ESI+, ESI- Switch -> diverse scan ranges possible (Report Header)<br>scan range 100-1000 m/z<br>scan range 160-1000 m/z<br>scan range 160-2000 m/z |

Preparative HPLC Conditions B:

"Purification by preparative HPLC" in the subsequent specific experimental descriptions refers to (unless otherwise noted) the following conditions:

Analytics:

| | |
|---|---|
| System: | Waters Aqcuity UPLC-MS: Binary Solvent Manager, Sample Manager/Organizer, Column Manager, PDA, ELSD, SQD 3001 |
| Column: | Aqcuity BEH C18 1.7 50 x 2.1 mm |
| Solvent: | A = H$_2$O + 0.1% HCOOH<br>B = Acetonitril |
| Gradient: | 0-1.6 min 1-99% B, 1.6-2.0 min 99% B |
| Flow: | 0.8 mL/min |
| Temperature: | 60° C. |
| Injection: | 2.0 µl |
| Detection: | DAD scan range 210-400 nm<br>MS ESI+, ESI-, scan range 160-1000 m/z<br>ELSD |

Preparation:

| | |
|---|---|
| System: | Waters Autopurificationsystem: Pump 2545, Sample Manager 2767, CFO, DAD 2996, ELSD 2424, SQD 3001 |
| Column: | XBrigde C18 5 µm 100 x 30 mm |
| Solvent: | A = H$_2$O + 0.1% HCOOH<br>B = Acetonitril |
| Gradient: | 0-1 min 1% B, 1-8 min 1-99% B, 8-10 min 99% B |
| Flow: | 50 mL/min |
| Temperature: | RT |
| Solution: | Max. 250 mg/2.5 mL DMSO o. DMF |
| Injection: | 1 x 2.5 mL |
| Detection: | DAD scan range 210-400 nm<br>MS ESI+, ESI-, scan range 160-1000 m/z |

Chiral HPLC Conditions C:

Chiral HPLC-data given in the subsequent specific experimental descriptions refer to the following conditions:

Analytics:

| | |
|---|---|
| System: | Dionex: Pump 680, ASI 100, Waters: UV-Detektor 2487 |
| Column: | Chiralpak IC 5 µm 150 x 4.6 mm |
| Solvent: | Hexan/Ethanol 80:20 + 0.1% Diethylamin |
| Flow: | 1.0 mL/min |
| Temperature: | 25° C. |
| Solution: | 1.0 mg/mL EtOH/MeOH 1:1 |
| Injection: | 5.0 µl |
| Detection: | UV 280 nm |

Preparation:

| | |
|---|---|
| System: | Agilent: Prep 1200, 2xPrep Pump, DLA, MWD, Prep FC, ESA: Corona |
| Column: | Chiralpak IC 5 µm 250 x 30 mm |
| Solvent: | Hexan/Ethanol 80:20 + 0.1% Diethylamin |
| Flow: | 40 mL/min |
| Temperature: | RT |
| Solution: | 660 mg/5.6 mL EtOH |
| Injection: | 8 x 0.7 mL |
| Detection: | UV 280 nm |

Flash Column Chromatography Conditions A

"Purification by (flash) column chromatography" as stated in the subsequent specific experimental descriptions refers to the use of Biotage Flashmaster II or Isolera (SP4) purification systems. For technical specifications see "Biotage product catalogue" on www.biotage.com.

Determination of Optical Rotation Conditions

Optical rotations were measured in DMSO, at 589 nm wavelength, 20° C., concentration 1.0000 g/100 ml, intergration time 10 s, film thickness 100.00 mm.

SYNTHETIC INTERMEDIATES

Intermediate 1.A

Preparation of 3,5-difluoro-N-(2-fluoro-4-iodophenyl)-2-nitroaniline

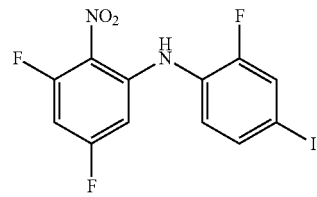 [SMILES: O=[N+]([O-])c1c(F)cc(F)cc1Nc1ccc(I)cc1F]

25 g 1,3,5-trifluoro-2-nitrobenzene (141.2 mmol, 1 eq.) and 33.5 g 2-fluoro-4-iodoaniline (141.2 mmol. 1 eq.) were dissolved in 250 mL dry THF and cooled with ice-salt to −10 to 0° C. upon which 424 mL lithium hexamethyldisilazide (LiHMDS) solution (1M in THF; 424 mmol, 3. eq.) were added slowly over a 1 h periode. Upon completion of addition of base, the reaction mixtures was allowed to warm to rt and stirring was continued for 5 days. The reaction mixture was quenched with 0.5 N hydrochloric acid and diluted with ethyl acetate. Saturated ammonium chloride solution was added to facilitate phase separation. The separated aqueous phase was reextracted twice with ethyl acetate. The combined organic layers were washed with brine, dried over sodium sulfate, filtered and concentrated in vacuo to give dark solid residue. The residue was purified by flash column chromatography on silica gel with hexane and hexane/ethyl acetate 8:2 as eluent to yield 45.8 gram (82% yield) of the analytically pure target compound as a slightly brownish solid.

$^1$H-NMR (d$_6$-DMSO; 400 MHz): δ=8.86 (s, 1H); 7.73 (dd, 1H); 7.55 (dd, 1H); 7.13 (t, 1H); 6.96 (ddd, 1H); 6.40-6.44 (m, 1H).

LC-MS: retention time: 1.5 min

MS ES$^+$: 392.9 [M−H]$^−$

Intermediate 2.A

Preparation of 3-(3-aminophenoxy)-5-fluoro-N-(2-fluoro-4-iodophenyl)-2-nitroaniline

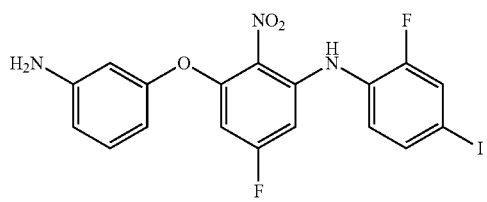 [SMILES: Nc1cccc(Oc2cc(F)cc(Nc3ccc(I)cc3F)c2[N+](=O)[O-])c1]

18.4 g 3,5-difluoro-N-(2-fluoro-4-iodophenyl)-2-nitroaniline (46.9 mmol, 1. eq.), 5.6 g 3-amino phenol (51.6 mmol. 1.1 eq.) and 9.7 g potassium carbonate (70.3 mmol, 1.5 eq.) were weighed into a round-bottom flask. 300 mL dry DMF were added and the resulting slurry was stirred at rt for 3 days. The reaction mixture was quenched by addition of water and diluted with ethyl acetate and phases were separated. The separated aqueous layer was reextracted twice with ethyl acetate. The combined organic layers were washed with brine, dried over sodium sulfate, filtered and concentrated in vacuo. The residue was purified by flash column chromatography on silica gel with a gradient from pure hexane to hexane/ethyl acetate 1:1 as eluent to yield 11.6 g (51% yield) of the target compound which contained a minor amount of the regioisomeric 5-(3-aminophenoxy)-3-fluoro-N-(2-fluoro-4-iodophenyl)-2-nitroaniline. In general, this regioisomeric mixture was moved forward through the subsequent transformations and separation into the pure regioisomeric example compounds was done by preparative HPLC after the final transformations (see below).

$^1$H-NMR (d$_6$-DMSO; 300 MHz): δ=8.45 (s, 1H); 7.68 (dd, 1H); 7.52 (dd, 1H); 7.07 (t, 1H); 7.01 (t, 1H); 6.38 (dd, 1H); 6.26-6.31 (m, 1H); 6.16-6.24 (m, 3H); 5.34 (s, 2H).

LC-MS: retention time: 1.56 min
MS ES$^+$: 484.20 [M+H]$^+$

Intermediate 3.A

Preparation of N-(3-{5-fluoro-3-[(2-fluoro-4-iodophenyl)amino]-2-nitrophenoxy}-phenyl)ethanesulfonamide

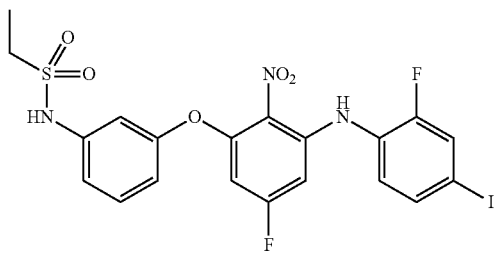

11.7 g 3-(3-aminophenoxy)-5-fluoro-N-(2-fluoro-4-iodophenyl)-2-nitroaniline (24.3 mmol, 1. eq.; containing a minor amount of the regioisomeric 5-(3-aminophenoxy)-3-fluoro-N-(2-fluoro-4-iodophenyl)-2-nitroaniline) was dissolved in 98 mL pyridine, set under an atmosphere of nitrogen and treated sequentially with 3.4 mL ethyl sulfonyl chloride (36.4 mmol, 1.5 eq.; dissolved in pyridine). The resulting reaction mixture was stirred at rt for 20 h after which LCMC analysis showed final turnover. The reaction mixture was quenched by addition of water and diluted with ethyl acetate and phases were separated. The separated aqueous layer was reextracted twice with ethyl acetate. The combined organic layers were washed with brine, dried over sodium sulfate, filtered and concentrated in vacuo to give 14.8 g of the crude target compound (which contained a minor amount of the regioisomeric N-(3-{3-fluoro-5-[(2-fluoro-4-iodophenyl)amino]-2-nitrophenoxy}-phenyl)ethanesulfonamide) which was used without further purification in the subsequent transformations.

$^1$H-NMR (d$_6$-DMSO; 300 MHz): δ=9.97 (s, 1H); 8.52 (s, 1H); 7.70 (dd, 1H); 7.52 (br. d, 1H); 7.34 (t, 1H); 7.10 (t, 1H); 7.04 (dd, 1H); 6.92 (s, 1H); 6.79 (dd, 1H); 6.34-6.39 (m, 2H); 3.10 (q, 2H); 1.15 (t, 3H).

LC-MS: retention time: 1.49 min
MS ES$^+$: 576.01 [M+H]

Intermediate 4.A

Preparation of N-(3-{2-amino-5-fluoro-3-[(2-fluoro-4-iodophenyl)amino]phenoxy}-phenyl)ethanesulfonamide

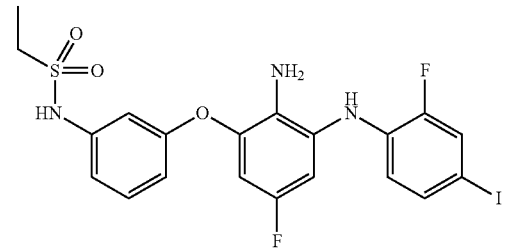 [SMILES: CCS(=O)(=O)Nc1cccc(Oc2cc(F)cc(Nc3ccc(I)cc3F)c2[N+](=O)[O-])c1]

14.8 g crude N-(3-{5-fluoro-3-[(2-fluoro-4-iodophenyl)amino]-2-nitrophenoxy}-phenyl)ethanesulfonamide (Intermediate 3.A) (25.9 mmol, 1. eq.; containing a minor amount of the regioisomeric N-(3-{3-fluoro-5-[(2-fluoro-4-iodophenyl)amino]-2-nitrophenoxy}-phenyl)ethanesulfonamide) was dissolved in 560 mL THF, heated to 50° C. (bath temperature) and treated within 30 minutes with a solution of 76 g sodium dithionite (440 mmol, 17 eq.) in 420 mL water. Stirring at 50° C. bath temperature was continued for 150 min upon which LCMS analysis showed complete turnover. The reaction mixture was cooled to rt, THF was removed in vacuo and the residue was partitioned between saturated sodium bicarbonate solution and ethyl acetate. After phase separation, the separated aqueous layer was reextracted twice with ethyl acetate. The combined organic layers were washed with brine, dried over sodium sulfate, filtered and concentrated in vacuo to give the crude target compound. Flash column chromatography on silica gel with a hexane/methyl-tert-butyl ether gradient as eluent provided 11.8 g of the target compound (21.6 mmol, 84% yield), which contained a minor amount of the regioisomeric N-(3-{2-amino-3-fluoro-5-[(2-fluoro-4-iodophenyl)amino]phenoxy}-phenyl)ethanesulfonamide.

$^1$H-NMR (d$_6$-DMSO; 300 MHz): δ=9.85 (br. s, 1H); 7.52 (dd, 1H); 7.42 (s, 1H); 7.31 (br. d, 1H); 7.25 (t, 1H); 6.90 (dd, 1H); 6.84 (t, 1H); 6.55-6.65 (m, 3H); 6.48 (dd, 1H); 4.47 (s, 2H); 3.07 (q, 2H); 1.14 (t, 3H).

LC-MS: retention time: 1.46 min
MS ES$^+$: 546.14 [M+H]$^+$

Intermediate 5.A

Preparation of 3-(3-amino-2-methylphenoxy)-5-fluoro-N-(2-fluoro-4-iodophenyl)-2-nitroaniline

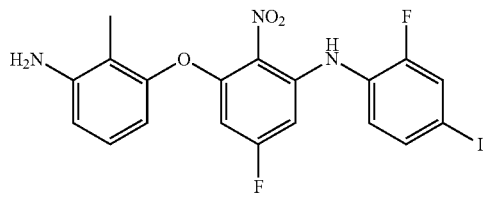 [SMILES: Cc1c(N)cccc1Oc1cc(F)cc(Nc2ccc(I)cc2F)c1[N+](=O)[O-]]

3.6 g of 3,5-difluoro-N-(2-fluoro-4-iodophenyl)-2-nitroaniline (Intermediate 1A; 9.2 mmol, 1 eq.), 1.1 g 3-amino-2-methyl phenol (9.2 mmol, 1 eq.) and 4.5 g caesium carbonate (13.8 mmol, 1.5 eq.) were suspended in 35 mL DMF and stirred at rt for 16 h. LCMS analysis showed complete turnover. The reaction mixture was diluted with ethyl acetate, quenched with saturated sodium chloride solution, the layers were separated and the aqueous layer was reextracted with ethyl acetate. The combined organic layers were dried, filtered and concentrated in vacuo. The crude product was purified by flash column chromatography (n-hexane/ethyl acetate gradient) providing 1.18 of the desired product (26% yield).

$^1$H-NMR (d$_6$-DMSO; 400 MHz): δ=8.44 (s, 1H); 7.69 (dd, 1H); 7.52 (dd, 1H); 7.08 (t, 1H); 6.92 (t, 1H); 6.53 (d, 1H); 6.19-6.24 (m, 2H); 5.84 (dd, 1H); 5.17 (s, 2H); 1.84 (s, 3H).

LC-MS: retention time: 1.67 min
MS ES$^+$: 497.8 [M+H]$^+$

Intermediate 6.A

Preparation of N-(3-{5-fluoro-3-[(2-fluoro-4-iodophenyl)amino]-2-nitrophenoxy}-2-methylphenyl)ethanesulfonamide

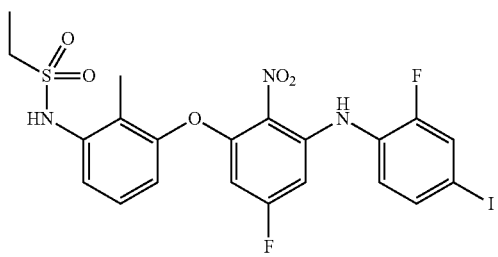

1.18 g 3-(3-amino-2-methylphenoxy)-5-fluoro-N-(2-fluoro-4-iodophenyl)-2-nitroaniline (2.3 mmol, 1 eq.) were dissolved in 9.6 mL pyridine, cooled to 0° C., treated with 292 µL ethyl sulfonyl chloride (3.1 mmol, 1.2 eq.) and stirred at 0° C. for 3 hours. The reaction mixture was diluted with toluene and concentrated in vacuo. The residue was partitioned between water and ethyl acetate. The aqueous layer was reextracted with ethyl acetate. The combined organic layers were dried, filtered and concentrated in vacuo to yield 1.6 g of the crude product, which was taken up in toluene and again concentrated in vacuo. The crude product was used in the subsequent transformations without further purification.

$^1$H-NMR (d$_6$-DMSO; 300 MHz): δ=9.25 (br. s, 1H); 8.51 (s, 1H); 7.70 (dd, 1H); 7.52 (dd, 1H); 7.05-7.26 (3H; obscured by residual toluene); 6.95 (dd, 1H); 6.26-6.31 (m, 1H); 5.99 (dd, 1H); 3.09 (q, 2H); 2.12 (s, 3H); 1.22 (t, 3H).

LC-MS: retention time: 1.48 min
MS ES$^-$: 587.9 [M–H]$^-$

Intermediate 7.A

Preparation of N-(3-{2-amino-5-fluoro-3-[(2-fluoro-4-iodophenyl)amino]phenoxy}-2-methylphenyl) ethanesulfonamide

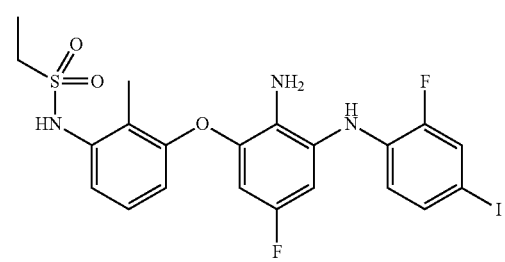 [SMILES: CCS(=O)(=O)Nc1cccc(Oc2cc(F)cc(Nc3ccc(I)cc3F)c2[N+](=O)[O-])c1C]

1.6 g crude N-(3-{5-fluoro-3-[(2-fluoro-4-iodophenyl)amino]-2-nitrophenoxy}-2-methylphenyl)-ethanesulfonamide (2.7 mmol, 1 eq.) were dissolved in 40 mL THF/EtOH 1:1 and treated with 3.1 g stannous chloride dihydrate (SnCl$_2$ 2H$_2$O) (13.6 mmol, 5 eq.) and the resulting mixture was refluxed for 16 h. The reaction mixture was concentrated, the residue quenched with 26% NH$_3$ and extracted with DCM. The combined organic layers were washed with ammonium chloride solution and saturated sodium chloride solution, dried, filtered and concentrated in vacuo. The residue was purified by flash column chromatography to give 996 mg of the target compound (65% yield).

$^1$H-NMR (d$_6$-DMSO; 300 MHz): δ=9.18 (br. s, 1H); 7.51 (dd, 1H); 7.40 (s, 1H); 7.32 (br. d, 1H); 7.15 (t, 1H); 7.06 (d, 1H); 6.68 (dd, 1H); 6.61 (t, 1H); 6.51 (dd, 1H); 6.18 (dd, 1H); 4.51 (s, 2H); 3.07 (q, 2H); 2.19 (s, 3H); 1.23 (t, 3H).

LC-MS: retention time: 1.47 min
MS ES$^+$: 560.14 [M+H]$^+$

Intermediate 8.A

Preparation of tert-butyl(3-{5-fluoro-3-[(2-fluoro-4-iodophenyl)amino]-2-nitrophenoxy}phenyl)carbamate

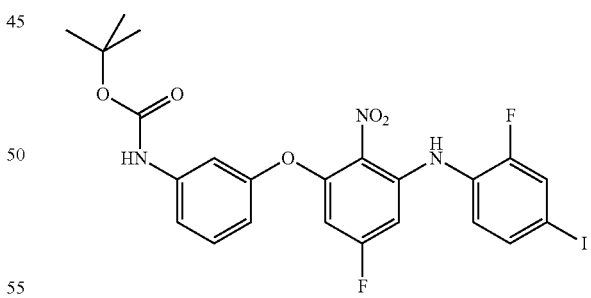

3.0 g of 3,5-difluoro-N-(2-fluoro-4-iodophenyl)-2-nitroaniline (Intermediate 1A; 70% pure, 5.3 mmol, 1 eq.), 1.1 g N-Boc-3-amino-phenol (5.3 mmol, 1 eq.) and 3.4 g caesium carbonate (10.7 mmol, 1.5 eq.) were suspended in 30 mL DMF and stirred at rt for 16 h. LCMS analysis showed complete turnover. The reaction mixture was partitioned between water and ethyl acetate, the layers were separated and the aqueous layer was reextracted with ethyl acetate. The combined organic layers were dried, filtered and concentrated in vacuo. The crude product was purified by flash column chromatography (n-hexane/ethyl acetate gradient) providing 1.35 of the desired product (44% yield).

¹H-NMR (d₆-DMSO; 300 MHz): δ=9.50 (s, 1H); 8.48 (s, 1H); 7.69 (dd, 1H); 7.52 (dd, 1H); 7.22-7.32 (m, 3H); 7.09 (t, 1H); 6.69 (dt, 1H); 6.30-6.36 (m, 1H); 6.26 (dd, 1H); 1.43 (s, 9H).
LC-MS: retention time: 1.68 min
MS ES⁻: 582.0 [M–H]⁻

Intermediate 9.A

Preparation of tert-butyl(3-{2-amino-5-fluoro-3-[(2-fluoro-4-iodophenyl)amino]phenoxy}phenyl)carbamate

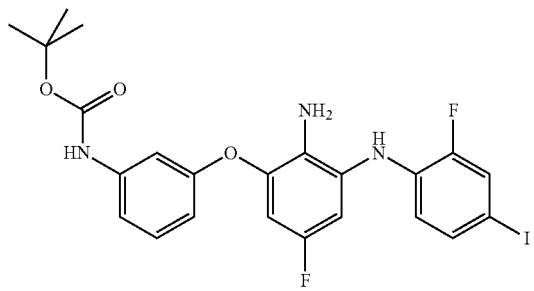 [SMILES: CC(C)(C)OC(=O)Nc1cccc(Oc2cc(F)cc(Nc3ccc(I)cc3F)c2N)c1]

1.35 g of tert-butyl(3-{5-fluoro-3-[(2-fluoro-4-iodophenyl)amino]-2-nitrophenoxy}phenyl)carbamate (2.3 mmol, 1 eq.) were dissolved in 43 mL THF and heated to 50° C. upon which a solution of 6.8 g sodium dithionite (39 mmol, 17 eq.) in 35 mL water was added and stirring was continued at that temperature for 1 h. The layers were separated and the aqueous layer was reextracted with ethyl acetate. The combined organic layers were dried, filtered and concentrated in vacuo. The crude product (1.5 g) was used without further purification.
¹H-NMR (d₆-DMSO; 300 MHz): δ=9.39 (s, 1H); 7.51 (dd, 1H); 7.41 (s, 1H); 7.31 (d, 1H); 7.09-7.23 (m, 3H); 6.52-6.62 (m, 3H); 6.41 (dd, 1H); 4.42 (s, 2H); 1.42 (s, 9H).
LC-MS: retention time: 1.62 min
MS ES⁺: 553.9 [M+H]⁺

Intermediate 10.A

Preparation of tert-butyl(3-{2-[(cyclopropylsulfonyl)amino]-5-fluoro-3-[(2-fluoro-4-iodophenyl)amino]phenoxy}phenyl)carbamate

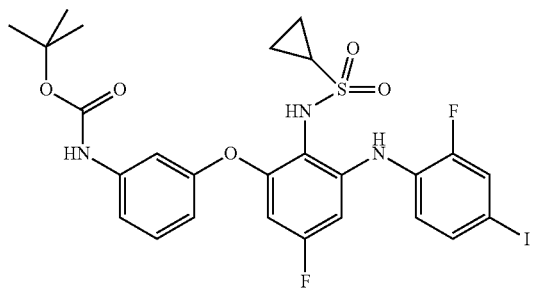 [SMILES: CC(C)(C)OC(=O)Nc1cccc(Oc2cc(F)cc(Nc3ccc(I)cc3F)c2NS(=O)(=O)C2CC2)c1]

1.5 g of crude tert-butyl(3-{2-amino-5-fluoro-3-[(2-fluoro-4-iodophenyl)amino]phenoxy}phenyl)carbamate (2.7 mmol, 1 eq.) were dissolved in 10 mL pyridine and 457 mg cyclopropyl sulfonyl chloride (3.3 mmol, 1.2 eq.) and stirring was continued at that temperature for 16 h. The reaction mixture was diluted with toluene and concentrated in vacuo. The residue was partitioned between DCM and water, the aqueous layer was reextracted with DCM. The combined organic layers were dried, filtered and concentrated in vacuo. The crude product was purified by flash column chromatography yielding 1.19 g of the target compound (67% yield).
¹H-NMR (d₆-DMSO; 300 MHz): δ=9.47 (s, 1H); 9.11 (br. s, 1H); 7.64 (dd, 1H); 7.57 (s, 1H); 7.44 (d, 1H); 7.23-7.31 (m, 3H); 7.12 (t, 1H); 6.68-6.73 (m, 1H); 6.55 (dd, 1H); 6.04 (dd, 1H); 2.60-2.70 (m, 1H); 1.42 (s, 9H); 0.80-0.90 (m, 4H).
LC-MS: retention time: 1.63 min
MS ES⁻: 655.9 [M–H]⁻

Intermediate 11.A

Preparation of N-{2-(3-aminophenoxy)-4-fluoro-6-[(2-fluoro-4-iodophenyl)amino]phenyl}cyclopropanesulfonamide

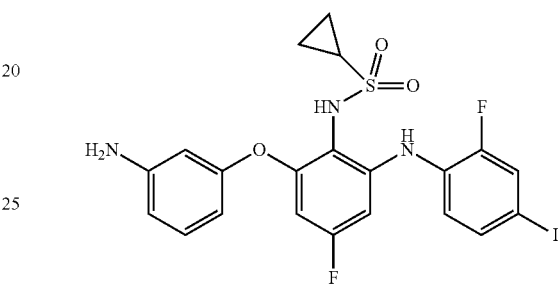

1.19 g of tert-butyl(3-{2-[(cyclopropylsulfonyl)amino]-5-fluoro-3-[(2-fluoro-4-iodophenyl)amino]phenoxy}phenyl)carbamate (1.8 mmol, 1 eq.) were dissolved in 15 mL DCM, treated with 2 mL TFA and stirred at rt for 6 h. The reaction mixture was cooled to 0° C. and adjusted with 1N Sodium hydroxide to pH 10. The layers were separated, the aqueous layer was reextracted with DCM. The combined organic layers were dried, filtered and concentrated in vacuo to yield 776 mg of the crude product (77% yield), which was used without further purification.
¹H-NMR (d₆-DMSO; 400 MHz): δ=9.08 (br. s, 1H); 7.63 (dd, 1H); 7.53 (s, 1H); 7.44 (d, 1H); 7.11 (t, 1H); 7.02 (t, 1H); 6.53 (dd, 1H); 6.38 (dd, 1H); 6.28 (t, 1H); 6.22 (dd, 1H); 6.03 (dd, 1H); 5.29 (s, 2H); 2.60-2.67 (m, 1H); 0.81-0.91 (m, 4H).
LC-MS: retention time: 1.46 min
MS ES⁺: 557.8 [M+H]⁺

Intermediate 12.A

Preparation of 3-(3-amino-4-fluorophenoxy)-5-fluoro-N-(2-fluoro-4-iodophenyl)-2-nitroaniline

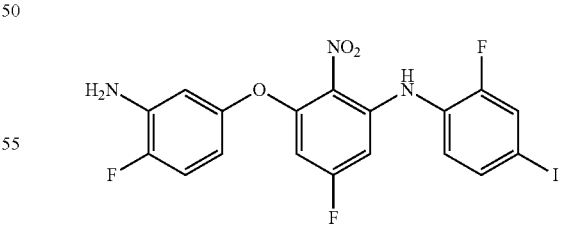

1 g of 3,5-difluoro-N-(2-fluoro-4-iodophenyl)-2-nitroaniline (Intermediate 1A; 2.537 mmol, 1 eq.), 194 mg 3-amino-4-fluorophenol (1.522 mmol, 0.6 eq.) and 1.240 g caesium carbonate (3.806 mmol, 1.5 eq.) were suspended in 12 mL DMF and stirred at rt for 72 h. The reaction mixture was partitioned between butan-2-one and half saturated brine. The layers were separated and the aqueous layer was reextracted twice with ethyl butan-2-one. The combined organic layers were washed with brine, dried, filtered and concentrated in vacuo. The crude product was purified by flash column chromatography (n-hexane/ethyl acetate gradient) providing 450 mg of a mixture of the desired product with its para regioisomer that eluted with the same retention time (63% UV purity). This material was used without further purification.

LC-MS: retention time: 1.54 min
MS ES+: 502.39 [M+H]+

Intermediate 13.A

Preparation of N-(2-fluoro-5-{5-fluoro-3-[(2-fluoro-4-iodophenyl)amino]-2-nitrophenoxy}phenyl)sulfuric diamide

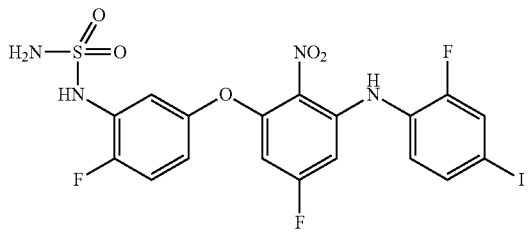 [SMILES: NS(=O)(=O)Nc1cc(Oc2cc(F)cc(Nc3ccc(I)cc3F)c2[N+](=O)[O-])ccc1F]

Solution A: 254 mg chlorsulfonyl isocyanate (1.797 mmol, 2 eq.) were dissolved in 0.427 mL DCM, the mixture heated to 40° C. and then treated with formic acid and treated with 71 μL formic acid (1.887 mmol, 2.1 eq.) and 1.3 μl DMA (0.014 mmol, 0.016 eq.) dropwise while gas evolution occurred. The mixture was heated to reflux for another 15 minutes.

450 mg crude 3-(3-amino-4-fluorophenoxy)-5-fluoro-N-(2-fluoro-4-iodophenyl)-2-nitroaniline (0.898 mmol, 1 eq.) were dissolved in 3.5 mL DMA, and treated with 235 μL DIPEA (1.348 mmol, 1.5 eq.). Upon cooling to 0° C., solution A was added dropwise and the resulting mixture was stirred at rt for 18 h. The reaction mixture was partitioned between water and ethyl ether and the aqueous layer was reextracted twice with ethyl ether. The combined organic layers were washed once with half saturated brine, once with brine, dried, filtered and concentrated in vacuo, providing 597 mg of crude product containing a mixture of the target compound and its para regioisomer (71% ortho, 11% para) which was used in the subsequent transformations without further purification.

LC-MS: retention time: 1.40 min
MS ES+: 581.27 [M+H]+

Intermediate 14.A

Preparation of N-(5-{2-amino-5-fluoro-3-[(2-fluoro-4-iodophenyl)amino]phenoxy}-2-fluorophenyl)sulfuric diamide

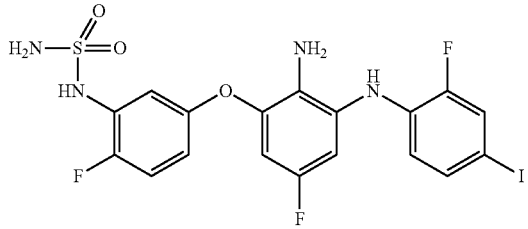 [SMILES: Nc1c(Nc2ccc(I)cc2F)cc(F)cc1Oc1ccc(F)c(NS(N)(=O)=O)c1]

597 mg crude N-(2-fluoro-5-{5-fluoro-3-[(2-fluoro-4-iodophenyl)amino]-2-nitrophenoxy}phenyl)sulfuric diamide (1.028 mmol, 1 eq.) were dissolved in 20 mL THF, warmed to 50° C., treated with a solution of 3.044 g sodium dithionite (17.484 mmol, 17 eq.) in 16 ml of water dropwise over a period of 30 minutes. The resulting mixture was stirred at this temperature for another 5 h. Upon cooling to rt the phases separated. The organic layer was separated, concentrated in vacuo and redissolved in ethyl acetate. The aqueous layer was diluted with saturated sodium bicarbonate solution and then extracted twice with ethyl acetate. The combined organic layers were washed once with half saturated brine and once with brine saturated, dried, filtered and concentrated in vacuo, providing 547 mg of crude product which was used in the subsequent transformations without further purification.

LC-MS: retention time: 1.34 min
MS ES+: 551.41 [M+H]+

Intermediate 15.A

Preparation of tert-butyl [(3-hydroxybenzyl)sulfamoyl]carbamate

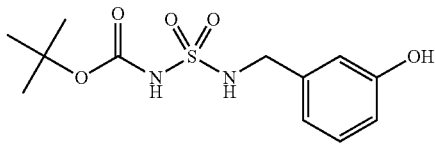 [SMILES: CC(C)(C)OC(=O)NS(=O)(=O)NCc1cccc(O)c1]

Solution A: 6,321 g chlorosulfonyl isocyanate (44.659 mmol, 1.1 eq.) were dissolved in 60 ml dry dichloromethane. A solution of tert. butanol in 30 ml dry dichloromethane was added at rt and stirred for another 5 min.

Solution B: 5 g 3-(aminomethyl)phenol (40.599 mmol, 1 eq.) were suspended in 110 mL dry dichloromethane, 6,791 ml triethylamine (48.719 mmol, 1.2 eq.) were added and the mixture was cooled to 0° C. upon which solution A was added dropwise. Stirring at rt was continued for 1 h.

The reaction mixture was quenched by addition of half concentrated ammonium chloride solution, diluted with dichloromethane and phases were separated. The separated aqueous phase was reextracted twice with dichloromethane. The combined organic layers were washed with brine, dried over sodium sulfate, filtered and concentrated in vacuo to give the crude product. The residue was purified by crystallization to yield 6.469 gram (53% yield) of the target compound.

1H-NMR (d6-DMSO; 300 MHz): δ=10.79 (br. s, 1H); 9.30 (s, 1H); 8.04 (dd, 1H); 7.05 (dd, 1H); 6.72-6.65 (m, 2H); 6.59 (dm, 1H); 3.89 (d, 2H); 1.37 (s, 9H).

LC-MS: retention time: 0.88 min
MS ES−: 301.2 [M−H]−

Intermediate 16.A

Preparation of tert-butyl [(3-{5-fluoro-3-[(2-fluoro-4-iodophenyl)amino]-2-nitrophenoxy}benzyl)sulfamoyl]carbamate

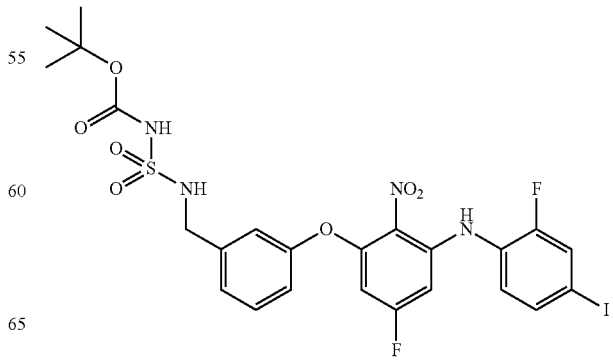

2.0 g of 3,5-difluoro-N-(2-fluoro-4-iodophenyl)-2-nitroaniline (Intermediate 1A; 64% pure, 3.25 mmol, 1 eq.), 0.98 g tert-butyl [(3-hydroxybenzyl)sulfamoyl]carbamate (Intermediate 2A; 3.24 mmol, 1 eq.) and 1.6 g caesium carbonate (4.9 mmol, 1.5 eq.) were suspended in 25 mL DMF and stirred in a closed vial at rt for 3 days. Additional 0.4 eq. tert-butyl [(3-hydroxybenzyl)sulfamoyl]carbamate and 0.4 eq. caesium carbonate were added and stirring was continued for 2 days. The reaction mixture was partitioned between sodium chloride solution and ether, the layers were separated and the aqueous layer was reextracted with ether. The combined organic layers were dried, filtered and concentrated in vacuo to yield 3.08 g of the crude product (as a regioisomeric mixture containing some unreacted starting material), which was used in the subsequent reaction without further purification.

LC-MS: retention time: 1.55 min

MS ES⁻: 674.8 [M−H]⁻

Intermediate 17.A

Preparation of tert-butyl [(3-{2-amino-5-fluoro-3-[(2-fluoro-4-iodophenyl)amino]phenoxy}benzyl)sulfamoyl]carbamate

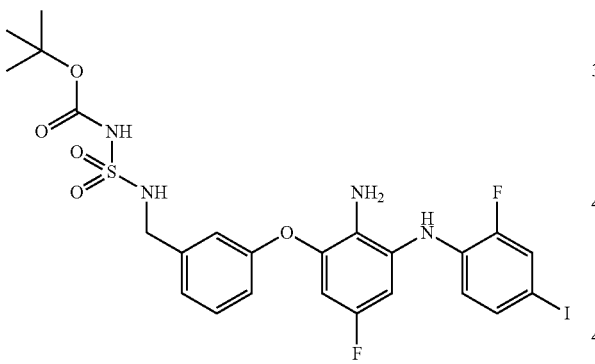

3.08 g of tert-butyl [(3-{5-fluoro-3-[(2-fluoro-4-iodophenyl)amino]-2-nitrophenoxy}benzyl)sulfamoyl]carbamate (4.55 mmol, 1 eq.) were dissolved in 88 mL THF and heated to 50° C. upon which a solution of 13.5 g sodium dithionite (77.4 mmol, 17 eq.) in 70 mL water was added and stirring was continued at that temperature for 5 h. The layers were separated and the THF layer was concentrated in vacuo. The residue was taken up in ethyl acetate, washed with sodium bicarbonate solution and sodium chloride solution, dried, filtered and concentrated in vacuo. The residue was further purified by flash column chromatography (hexan to hexan/ethyl acetate 1:1 gradient) to yield 886 mg (30% yield) of the target compound (as a 2-3:1 regioisomeric mixture).

LC-MS: retention time: 1.51 min

MS ES⁺: 646.9 [M+H]⁺

Intermediate 18.A

Preparation of tert-butyl [(3-{2-[(cyclopropylsulfonyl)amino]-5-fluoro-3-[(2-fluoro-4-iodophenyl)amino]phenoxy}benzyl)sulfamoyl]carbamate

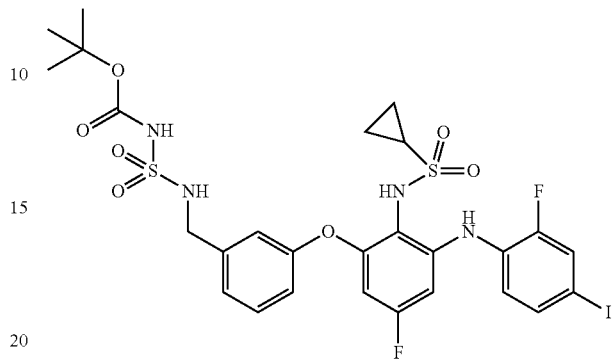

864 mg of crude tert-butyl [(3-{2-amino-5-fluoro-3-[(2-fluoro-4-iodophenyl)amino]phenoxy}benzyl)sulfamoyl]carbamate (1.37 mmol, 1 eq.) were dissolved in 13 mL pyridine and 250 mg cyclopropyl sulfonyl chloride (1.78 mmol, 1.3 eq.) and stirring was continued at that temperature for 16 h. The reaction mixture was diluted with toluene and concentrated in vacuo. The residue was partitioned between ethyl acetate and water, the aqueous layer was reextracted with ethyl acetate. The combined organic layers were dried, filtered and concentrated in vacuo. The residue was further purified by flash column chromatography (hexan to hexan/ethyl acetate 1:1 gradient) to yield 814 mg of the target compound (70% UV-purity), which was used for the subsequent transformation.

LC-MS: retention time: 1.52 min

MS ES⁻: 748.8 [M−H]⁻

EXAMPLE COMPOUNDS

Example 1

Preparation of N-(2-{3-[(ethylsulfonyl)amino]phenoxy}-4-fluoro-6-[(2-fluoro-4-iodophenyl)amino]phenyl)cyclopropanesulfonamide

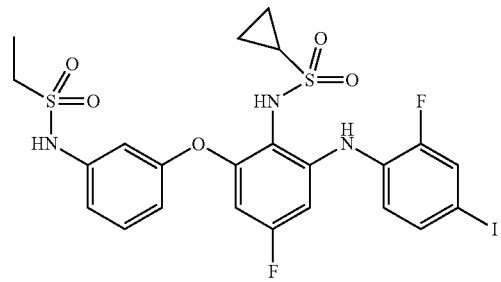 [SMILES: CCS(=O)(=O)Nc1cccc(Oc2cc(F)cc(Nc3ccc(I)cc3F)c2NS(=O)(=O)C2CC2)c1]

154 mg N-(3-{2-amino-5-fluoro-3-[(2-fluoro-4-iodophenyl)amino]phenoxy}-phenyl)ethanesulfonamide (Intermediate 4.A) (0.28 mmol, 1. eq.; containing a minor amount of the regioisomeric N-(3-{2-amino-3-fluoro-5-[(2-fluoro-4-iodophenyl)amino]phenoxy}-phenyl)ethanesulfonamide) was dissolved in 1 mL pyridine and treated with 79.4 mg cyclopropanesulfonyl chloride (0.565 mmol, 2 eq.). The reaction mixture was stirred at rt for 48 h. The reaction mixture was quenched with water and extracted several times with dichloromethane. The combined organic layers were washed with brine, filtered and concentrated in vacuo to give the crude target compound. Preparative HPLC purification provided 62 mg of the analytically pure target compound (0.09 mmol, 32% yield).

$^1$H-NMR (d$_6$-DMSO; 300 MHz): δ=9.92 (br. s, 1H); 9.09 (br. s, 1H); 7.64 (dd, 1H); 7.59 (br. s, 1H); 7.45 (br. d, 1H); 7.34 (t, 1H); 7.12 (t, 1H); 7.00-7.04 (m, 1H); 6.96 (t, 1H); 6.81 (dd, 1H); 6.57 (dd, 1H); 6.15 (dd, 1H); 3.10 (q, 2H); 2.63-2.71 (m, 1H); 1.15 (t, 3H); 0.82-0.88 (m, 4H).

LC-MS: retention time: 1.51 min
MS ES$^+$: 650.17 [M+H]$^+$

The following example compounds 2 to 5 were prepared in analogy to example compound 1 by treating N-(3-{2-amino-5-fluoro-3-[(2-fluoro-4-iodophenyl)amino]phenoxy}-phenyl)-ethanesulfonamide (Intermediate 4.A) with the respective commercially available sulfonyl chlorides in the presence of pyridine.

| Example | Structure | Name | Analytical Data |
| --- | --- | --- | --- |
| 2 | 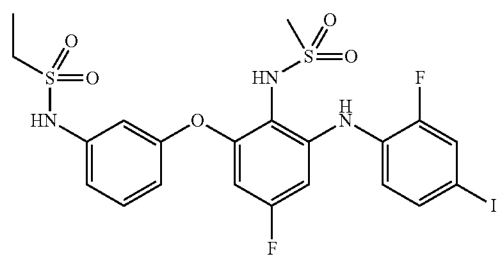 [SMILES: CCS(=O)(=O)Nc1cccc(Oc2cc(F)cc(Nc3ccc(I)cc3F)c2NS(C)(=O)=O)c1] | N-(3-{5-fluoro-3-[(2-fluoro-4-iodophenyl)amino]-2-[(methylsulfonyl)amino]phenoxy}-phenyl)ethanesulfonamide | $^1$H-NMR (d$_6$-DMSO; 300 MHz): δ = 9.92 (br. s, 1 H); 9.12 (br. s, 1 H); 7.65 (dd, 1 H); 7.59 (s, 1 H); 7.45 (br. d, 1 H); 7.34 (t, 1 H); 7.11 (t, 1 H); 7.00-7.04 (m, 1 H); 6.96 (t, 1 H); 6.82 (dd, 1 H); 6.53 (dd, 1 H); 6.14 (dd, 1 H); 3.10 (q, 2 H); 3.00 (s, 3 H); 1.15 (t, 3 H). LC-MS: retention time: 1.39 min MS ES$^+$: 623.7 [M + H]$^+$ |
| 3 | 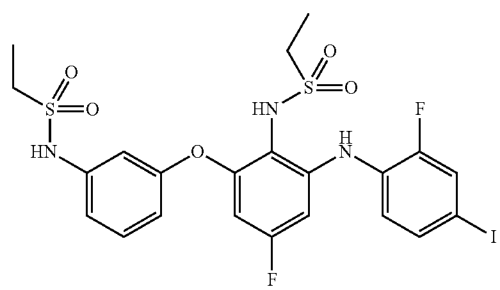 [SMILES: CCS(=O)(=O)Nc1cccc(Oc2cc(F)cc(Nc3ccc(I)cc3F)c2NS(=O)(=O)CC)c1] | N-(3-{2-[(ethylsulfonyl)amino]-5-fluoro-3-[(2-fluoro-4-iodophenyl)amino]-phenoxy}phenyl)-ethanesulfonamide | $^1$H-NMR (d$_6$-DMSO; 300 MHz): δ = 9.93 (br. s, 1 H); 9.08 (br. s, 1 H); 7.65 (dd, 1 H); 7.58 (s, 1 H); 7.44 (br. d, 1 H); 7.34 (t, 1 H); 7.09 (t, 1 H); 7.02 (dd, 1 H); 6.95 (t, 1 H); 6.80 (dd, 1 H); 6.58 (dd, 1 H); 6.17 (dd, 1 H); 3.10 (br. q, 4 H); 1.19 (t, 3 H); 1.15 (t, 3 H). LC-MS: retention time: 1.43 min MS ES$^+$: 637.8 [M + H]$^+$ |
| 4 | 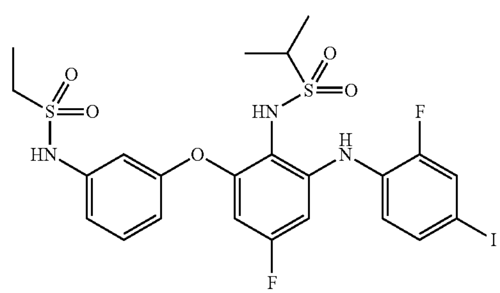 [SMILES: CCS(=O)(=O)Nc1cccc(Oc2cc(F)cc(Nc3ccc(I)cc3F)c2NS(=O)(=O)C(C)C)c1] | N-(2-{3-[(ethylsulfonyl)amino]phenoxy}-4-fluoro-6-[(2-fluoro-4-iodophenyl)amino]phenyl)propane-2-sulfonamide | $^1$H-NMR (d$_6$-DMSO; 300 MHz): δ = 9.94 (br. s, 1 H); 9.02 (br. s, 1 H); 7.65 (dd, 1 H); 7.56 (s, 1 H); 7.44 (br. d, 1 H); 7.34 (t, 1 H); 7.09 (t, 1 H); 7.02 (dd, 1 H); 6.94 (t, 1 H); 6.80 (dd, 1 H); 6.64 (dd, 1 H); 6.19 (dd, 1 H); 3.25 (m, 1 H); 3.10 (q, 2 H); 1.24 (d, 6 H); 1.15 (t, 3 H). LC-MS: retention time: 1.46 min MS ES$^+$: 651.9 [M + H]$^+$ |
| 5 | 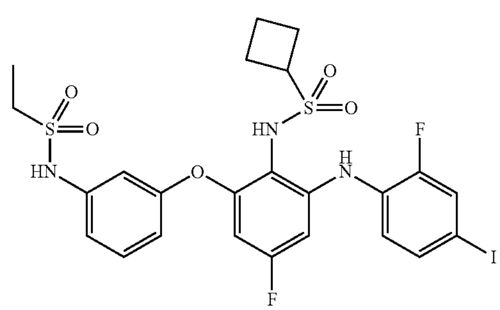 [SMILES: CCS(=O)(=O)Nc1cccc(Oc2cc(F)cc(Nc3ccc(I)cc3F)c2NS(=O)(=O)C2CCC2)c1] | N-(2-{3-[(ethylsulfonyl)amino]phenoxy}-4-fluoro-6-[(2-fluoro-4-iodophenyl)amino]phenyl)cyclobutane-sulfonamide | $^1$H-NMR (d$_6$-DMSO; 300 MHz): δ = 9.94 (br. s, 1 H); 9.01 (br. s, 1 H); 7.65 (dd, 1 H); 7.58 (s, 1 H); 7.44 (br. d, 1 H); 7.35 (t, 1 H); 7.09 (t, 1 H); 7.03 (dd, 1 H); 6.97 (t, 1 H); 6.83 (dd, 1 H); 6.59 (dd, 1 H); 6.13 (dd, 1 H); 3.92 (m, 1 H); 3.11 (q, 2H); 2.09-2.32 (m, 4H); 1.76-1.88 (m, 2 H); 1.15 (t, 3 H). LC-MS: retention time: 1.49 min MS ES$^+$: 663.8 [M + H]$^+$ |

Example 6

Preparation of N-(3-{5-fluoro-3-[(2-fluoro-4-iodophenyl)amino]-2-(sulfamoylamino)phenoxy}phenyl)ethanesulfonamide

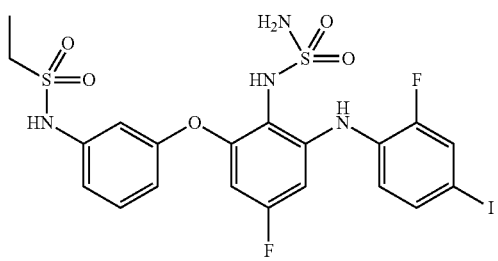 [SMILES: CCS(=O)(=O)Nc1cccc(Oc2cc(F)cc(Nc3ccc(I)cc3F)c2NS(N)(=O)=O)c1]

244 mg N-(3-{2-amino-5-fluoro-3-[(2-fluoro-4-iodophenyl)amino]phenoxy}-phenyl)ethanesulfonamide (0.448 mmol, 1 eq.) were dissolved in 10 mL DCM, treated with 0.781 mL DIPEA (4.5 mmol, 10 eq.) and 388 mg sulfamoyl chloride (3.36 mmol, 7.5 eq.) and the resulting solution stirred at rt for four days. The reaction mixture was portioned between ammonium chloride solution and DCM, the aqueous layer reextracted with DCM, the combined organic layers dried, filtered and concentrated in vacuo. Flash column chromatography provided 97 mg of the target compound (35% yield). A second product fraction was further purified by thick layer chromatography (hexane/ethyl acetate 1:1 as eluent) yielding additional 67 mg of the target compound (22% yield).

$^1$H-NMR (d$_6$-DMSO; 400 MHz): δ=9.94 (br. s, 1H); 8.58 (br. s, 1H); 7.60-7.63 (m, 2H); 7.46 (br. d, 1H); 7.32 (t, 1H); 7.14 (t, 1H); 6.96-7.02 (m, 4H); 6.82 (dd, 1H); 6.48 (dd, 1H); 6.01 (dd, 1H); 3.10 (q, 2H); 1.16 (t, 3H).

LC-MS: retention time: 1.37 min
MS ES$^+$: 624.7 [M+H]$^+$

Example 7

Preparation of N-(2-{3-[(ethylsulfonyl)amino]-2-methylphenoxy}-4-fluoro-6-[(2-fluoro-4-iodophenyl)amino]phenyl)cyclopropanesulfonamide

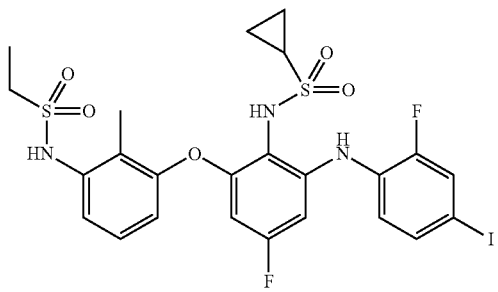 [SMILES: CCS(=O)(=O)Nc1cccc(Oc2cc(F)cc(Nc3ccc(I)cc3F)c2NS(=O)(=O)C2CC2)c1C]

185 mg N-(3-{2-amino-5-fluoro-3-[(2-fluoro-4-iodophenyl)amino]phenoxy}-2-methylphenyl)ethanesulfonamide (0.33 mmol, 1 eq.) were dissolved in 3 mL pyridine, and treated with 49 mg cyclopropyl sulfonyl chloride (0.33 mmol, 1 eq.) and stirred at it for 16 h. Further 15 mg cyclopropyl sulfonyl chloride were added and stirring was continued for 4 h. Additional 15 mg cyclopropyl sulfonyl chloride were added and stirring was continued overnight. The reaction mixture was quenched with water, diluted with toluene and concentrated in vacuo. The residue was portioned between water and ethyl acetate, the aqueous layer reextracted with ethyl acetate, the combined organic layers dried, filtered and concentrated in vacuo. Flash column chromatography provided 150 mg of the target compound (64% yield).

$^1$H-NMR (d$_6$-DMSO; 300 MHz): δ=9.16 (br. s, 2H); 7.62-7.65 (m, 2H); 7.45 (br. d, 1H); 7.11-7.24 (m, 3H); 6.90 (d, 1H); 6.51 (dd, 1H); 5.78 (dd, 1H); 3.10 (q, 2H); 2.67-2.70 (m, 1H); 2.15 (s, 3H); 1.23 (t, 3H); 0.83-0.86 (m, 4H).

LC-MS: retention time: 1.47 min
MS ES$^+$: 663.8 [M+H]$^+$

Example 8

Preparation of N-(3-{5-fluoro-3-[(2-fluoro-4-iodophenyl)amino]-2-(sulfamoylamino)phenoxy}-2-methylphenyl)ethanesulfonamide

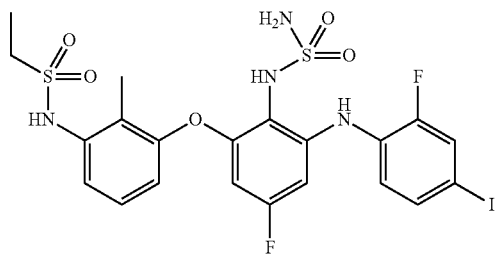 [SMILES: CCS(=O)(=O)Nc1cccc(Oc2cc(F)cc(Nc3ccc(I)cc3F)c2NS(N)(=O)=O)c1C]

Solution A: 65 mg Chlorsulfonylisocyanate were dissolved in 0.11 mL DCM, heated to reflux and treated with 18 μL formic acid and 350 μL DMA.

140 mg N-(3-{2-amino-5-fluoro-3-[(2-fluoro-4-iodophenyl)amino]phenoxy}-2-methylphenyl)ethanesulfonamide (0.233 mmol, 1 eq.) were dissolved in 0.79 mL DMA, and treated with 61 μL DIPEA. Solution A was added by syringe and the resulting mixture was stirred at rt for 16 h. The reaction mixture was portioned between water and ethyl acetate, the aqueous layer reextracted with ethyl acetate, the combined organic layers dried, filtered and concentrated in vacuo. Flash column chromatography provided 53 mg of the target compound (34% yield).

$^1$H-NMR (d$_6$-DMSO; 400 MHz): δ=9.15 (br. s, 1H); 8.59 (br. s, 1H); 7.64-7.68 (m, 2H); 7.46 (br. d, 1H); 7.12-7.24 (m, 3H); 7.05 (s, 2H); 6.94 (d, 1H); 6.43 (dd, 1H); 5.64 (dd, 1H); 3.10 (q, 2H); 2.16 (s, 3H); 1.24 (t, 3H).

LC-MS: retention time: 1.35 min
MS ES$^-$: 636.9 [M−H]$^-$

Example 9

Preparation of N-(2-{3-[(ethylsulfonyl)amino]phenoxy}-6-[(4-ethynyl-2-fluorophenyl)amino]-4-fluorophenyl)cyclopropanesulfonamide

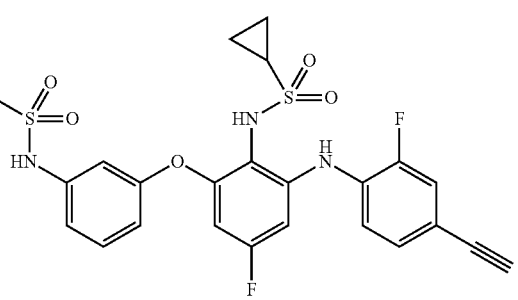

Step 1

100 mg N-(2-{3-[(ethylsulfonyl)amino]phenoxy}-4-fluoro-6-[(2-fluoro-4-iodophenyl)-amino]phenyl)cyclopropanesulfonamide (0.154 mmol, 1 eq.), 3.5 mg Pd(dba)$_2$ (0.006 mmol; 4 mol %), 1.2 mg copper (I) iodide (0.006 mmol; 4 mol %) and 8 mg triphenylphosphine (0.03 mmol; 20 mol %) are weighed into a microwave vial, dissolved in 1.5 mL triethylamine, set under an argon atmosphere and supplied with 128 µL trimethylsilyl acetylene (0.924 mmol, 6 eq.). The vial was capped and heated to 60° C. for 3 h upon which LCMS analysis showed complete turnover. The reaction mixture was concentrated in vacuo and the crude product was used without further purification.

LC-MS: retention time: 1.61 min

MS ES$^-$: 618.0 [M−H]$^-$

Step 2

The crude product from step 1 was dissolved in 2 mL THF and treated with 0.24 mL TBAF solution (1.0 M in THF; 0.24 mmol, 1.55 eq.) and stirred at rt for 16 h. The reaction mixture was diluted with ethyl acetate, washed with sat. sodium bicarbonate solution and subsequently with sat. sodium chloride solution, dried and filtered. After concentration in vacuo the residue was purified by preparative thin layer chromatography (5 DC plates 20×20 cm; hexane/ethyl acetate 1:1 as eluent) yielding 26 mg of the target compound (31% yield over 2 steps).

$^1$H-NMR (d$_6$-DMSO; 400 MHz): δ=9.92 (br. s, 1H); 9.14 (br. s, 1H); 7.75 (br. s, 1H); 7.38 (dd, 1H); 7.34 (dd, 1H); 7.28 (dd, 1H); 7.21 (dd, 1H); 7.02 (dd, 1H); 6.96 (dd, 1H); 6.81 (dd, 1H); 6.71 (dd, 1H); 6.21 (dd, 1H); 4.14 (s, 1H); 3.10 (q, 2H); 2.63 (m, 1H); 1.15 (t, 3H); 0.87-0.81 (m, 4H).

LC-MS: retention time: 1.35 min

MS ES$^+$: 548.0 [M+H]$^+$

Example 10

Preparation of N-(3-{3-[(4-ethynyl-2-fluorophenyl)amino]-5-fluoro-2-(sulfamoylamino)phenoxy}phenyl)ethanesulfonamide [Formic Acid salt]

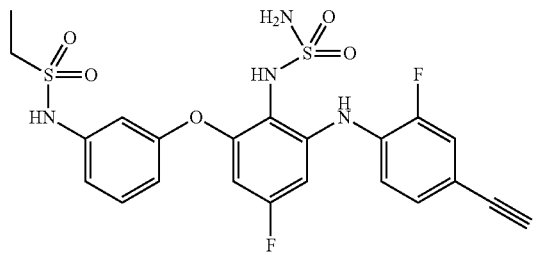 [SMILES: C#Cc1ccc(Nc2cc(F)cc(Oc3cccc(NS(=O)(=O)CC)c3)c2NS(N)(=O)=O)c(F)c1]

Step 1

100 mg N-(3-{5-fluoro-3-[(2-fluoro-4-iodophenyl)amino]-2-(sulfamoylamino)-phenoxy}phenyl)ethanesulfonamide (0.16 mmol, 1 eq.), 3.7 mg Pd(dba)$_2$ (0.006 mmol; 4 mol %), 1.2 mg CuI (0.006 mmol; 4 mol %) and 8.4 mg PPh$_3$ (0.03 mmol; 20 mol %) are weighed into a microwave vial, dissolved in 1.6 mL Et$_3$N, set under an Ar atmosphere and supplied with 133 µL trimethylsilyl acetylene (0.961 mmol, 6 eq.). The vial was capped and heated to 60° C. for 3 h upon which LCMS analysis showed complete turnover. The reaction mixture was concentrated in vacuo and the crude product (containing unreacted starting material) was used without further purification.

LC-MS: retention time: 1.52 min

MS ES$^-$: 593.4 [M−H]$^-$

Step 2

The crude product from step 1 was dissolved in 2 mL THF and treated with 0.24 mL TBAF solution (1.0 M in THF; 0.24 mmol, 1.55 eq.) and stirred at rt for 16 h. The reaction mixture was diluted with ethyl acetate, washed with sat. sodium bicarbonate solution and subsequently with sat. sodium chloride solution, dried and filtered. After concentration in vacuo the residue was purified by preparative HPLC purification yielding 2.2 mg of the target compound (3% yield over 2 steps).

$^1$H-NMR (d$_6$-DMSO; 300 MHz): δ=8.61 (br. s, 1H); 7.82 (s, 1H); 7.10-7.40 (m, 5H); 6.99-7.05 (m, 4H); 6.83 (d, 1H); 6.62 (d, 1H); 6.07 (dd, 1H); 4.15 (s, 1H); 3.10 (q, 2H); 1.16 (t, 3H).

LC-MS: retention time: 1.44 min

MS ES$^+$: 545.8 [M+HCO$_2$H]$^+$

Example 11

Preparation of N-{4-fluoro-2-[(2-fluoro-4-iodophenyl)amino]-6-[3-(sulfamoylamino)phenoxy]phenyl}cyclopropanesulfonamide

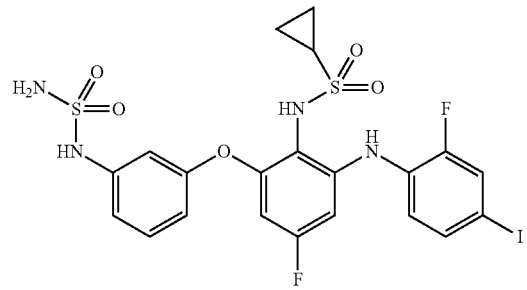 [SMILES: NS(=O)(=O)Nc1cccc(Oc2cc(F)cc(Nc3ccc(I)cc3F)c2NS(=O)(=O)C2CC2)c1]

Solution A: 63 mg Chlorsulfonylisocyanate were dissolved in 0.11 mL DCM, heated to reflux and treated with 18 µL formic acid and 340 µL DMA.

125 mg N-{2-(3-aminophenoxy)-4-fluoro-6-[(2-fluoro-4-iodophenyl)amino]phenyl}-cyclopropanesulfonamide (0.224 mmol, 1 eq.) were dissolved in 0.76 mL DMA, and treated with 47 µL DIPEA. Solution A was added by syringe and the resulting mixture was stirred at rt for 16 h. The reaction mixture was portioned between water and ethyl acetate, the aqueous layer reextracted with ethyl acetate, the combined organic layers dried, filtered and concentrated in vacuo. Flash column chromatography provided 77 mg of the target compound (34% yield).

$^1$H-NMR (d$_6$-DMSO; 400 MHz): δ=9.66 (br. s, 1H); 9.12 (br. s, 1H); 7.64 (dd, 1H); 7.58 (s, 1H); 7.44 (d, 1H); 7.29 (t, 1H); 7.15 (s, 2H); 7.11 (t, 1H); 6.99 (dd, 1H); 6.91 (t, 1H); 6.70 (dd, 1H); 6.56 (dd, 1H); 6.06 (dd, 1H); 2.62-2.69 (m, 1H); 0.81-0.90 (m, 4H).

LC-MS: retention time: 1.36 min

MS ES$^-$: 636.7 [M−H]$^-$

Example 12

Preparation of N-(4-fluoro-2-[(2-fluoro-4-iodophenyl)amino]-6-{3-[(isopropylsulfonyl)amino]phenoxy}phenyl)cyclopropanesulfonamide

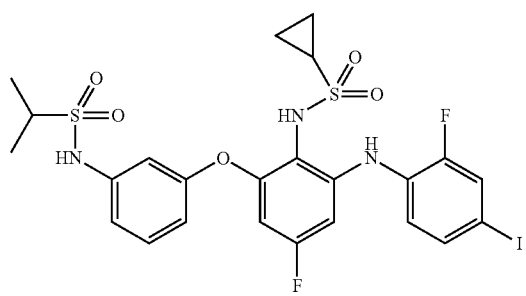 [SMILES: CC(C)S(=O)(=O)Nc1cccc(Oc2cc(F)cc(Nc3ccc(I)cc3F)c2NS(=O)(=O)C2CC2)c1]

125 mg N-{2-(3-aminophenoxy)-4-fluoro-6-[(2-fluoro-4-iodophenyl)amino]phenyl}-cyclopropanesulfonamide (0.22 mmol, 1 eq.) were dissolved in 1 mL pyridine, and treated with 31 µL isopropyl sulfonyl chloride (0.27 mmol, 1.2 eq.) and stirred at rt for 16 h. The reaction mixture was quenched with water, diluted with toluene and concentrated in vacuo. The residue was portioned between water and ethyl acetate, the aqueous layer reextracted with ethyl acetate, the combined organic layers dried, filtered and concentrated in vacuo. Preparative HPLC purification followed by flash column chromatography provided 70 mg of the target compound (47% yield).

$^1$H-NMR (d$_6$-DMSO; 400 MHz): δ=9.89 (br. s, 1H); 9.10 (br. s, 1H); 7.64 (dd, 1H); 7.59 (br. s, 1H); 7.44 (d, 1H); 7.32 (t, 1H); 7.12 (t, 1H); 7.03 (dd, 1H); 6.97 (t, 1H); 6.79 (dd, 1H); 6.57 (dd, 1H); 6.11 (dd, 1H); 3.21-3.28 (m, 1H); 2.61-2.67 (m, 1H); 1.20 (d, 6H); 0.80-0.88 (m, 4H).

LC-MS: retention time: 1.49 min

MS ES$^+$: 663.8 [M+H]$^+$

The following example compound 13 was prepared in analogy to example compound 12 by treating N-{2-(3-aminophenoxy)-4-fluoro-6-[(2-fluoro-4-iodophenyl)amino]phenyl}cyclopropanesulfonamide (Intermediate 11.A) with the respective commercially available sulfonyl chlorides in the presence of pyridine.

Example 14

Preparation of N-{4-fluoro-2-[(2-fluoro-4-iodophenyl)amino]-6-[4-fluoro-3-(sulfamoylamino)phenoxy]phenyl}cyclopropanesulfonamide

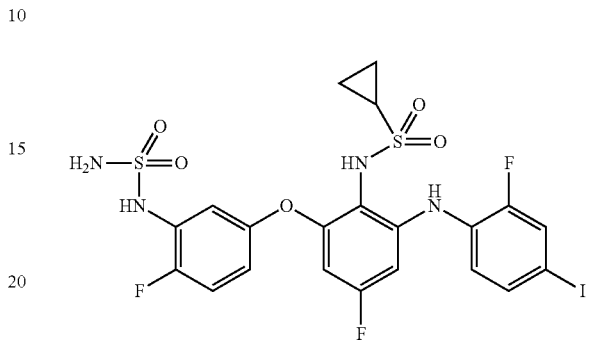

547 mg crude N-(5-{2-amino-5-fluoro-3-[(2-fluoro-4-iodophenyl)amino]phenoxy}-2-fluorophenyl)sulfuric diamide (Intermediate 14.A) (0.993 mmol, 1. eq.) was dissolved in 8.5 mL pyridine, cooled to 0° C. and treated with 140 mg cyclopropanesulfonyl chloride (0.993 mmol, 1 eq.). The reaction mixture was stirred at rt for 18 h. Another 70 mg of cyclopropanesulfonyl chloride (0.497 mmol, 0.5 eq.) were added and stirring was continued for 24 h. The reaction mixture diluted with toluene and concentrated in vacuo. The residue was partitioned between water and ethyl acetate and the aqueouse layer reextracted twice with ethyl acetate. The combined organic layers were washed once with half saturated brine and once with brine, filtered and concentrated in vacuo. The crude product was purified by flash column chromatography (n-hexane/ethyl acetate gradient) providing 40 mg of the desired product (6% yield).

$^1$H-NMR (d$_6$-DMSO; 400 MHz): δ=9.38 (br. s, 1H); 9.11 (br. s, 1H); 7.64 (dd, 1H); 7.58 (br. s, 1H); 7.44 (br. d, 1H); 7.28-7.22 (m, 2H); 7.17 (d, 2H); 7.11 (dd, 1H); 6.83 (dm, 1H); 6.55 (dd, 1H); 6.07 (dd, 1H); 2.71 (m, 1H); 0.89-0.82 (m, 4H).

LC-MS: retention time: 1.37 min

MS ES$^+$: 655.34 [M+H]$^+$

| Example | Structure | Name | Analytical Data |
|---|---|---|---|
| 13 | (structure shown) | N-(4-fluoro-2-[(2-fluoro-4-iodophenyl)amino]-6-{3-[(methylsulfonyl)amino]phenoxy}phenyl)cyclopropanesulfonamide | $^1$H-NMR (d$_6$-DMSO; 300 MHz): δ = 9.83 (br. s, 1 H); 9.16 (br. s, 1 H); 7.64 (dd, 1 H); 7.59 (s, 1 H); 7.45 (br. d, 1 H); 7.34 (dd, 1 H); 7.12 (dd, 1 H); 7.01 (br. d, 1 H); 6.93 (dd, 1 H); 6.82 (dd, 1 H); 6.57 (dd, 1 H); 6.16 (dd, 1 H); 2.99 (s, 3 H); 2.65 (m, 1 H); 0.88 - 0.78 (m, 4 H). LC-MS: retention time: 1.42 min MS ES$^+$: 635.8 [M + H]$^+$ |

Example 15

Preparation of N-(5-{2-[(cyclopropylsulfonyl)amino]-5-fluoro-3-[(2-fluoro-4-iodophenyl)amino]phenoxy}-2-fluorophenyl)cyclopropanesulfonamide

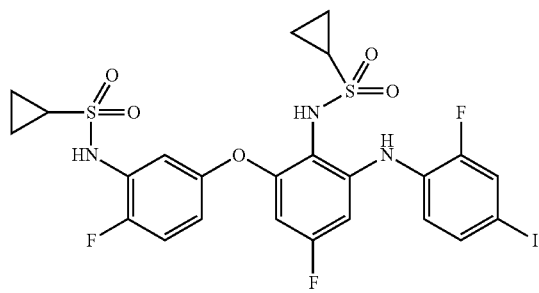 [SMILES: O=S(=O)(Nc1cc(Oc2cc(F)cc(Nc3ccc(I)cc3F)c2NS(=O)(=O)C2CC2)ccc1F)C1CC1]

26.06 mg (0.04 mmol, 4% yield) of N-(5-{2-[(cyclopropylsulfonyl)amino]-5-fluoro-3-[(2-fluoro-4-iodophenyl)amino]phenoxy}-2-fluorophenyl)cyclopropanesulfonamide were isolated as a side product from the reaction mixture for example compound 14.

$^1$H-NMR (d$_6$-DMSO; 300 MHz): δ=9.79 (br. s, 1H); 9.09 (br. s, 1H); 7.65 (dd, 1H); 7.60 (br. s, 1H); 7.45 (br. d, 1H); 7.31 (dd, 1H); 7.17-7.09 (m, 2H); 6.98 (m, 1H); 6.55 (dd, 1H); 6.08 (dd, 1H); 2.73-2.61 (m, 2H); 0.95-079 (m, 8H).

LC-MS: retention time: 1.44 min

MS ES$^+$: 679.7 [M+H]$^+$

Example 16

Preparation of N-(2-fluoro-5-{5-fluoro-3-[(2-fluoro-4-iodophenyl)amino]-2-(sulfamoylamino)phenoxy}phenyl)sulfuric diamide

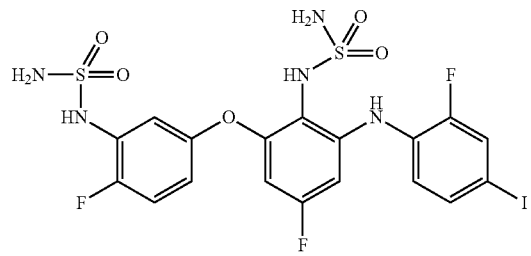 [SMILES: NS(=O)(=O)Nc1cc(Oc2cc(F)cc(Nc3ccc(I)cc3F)c2NS(N)(=O)=O)ccc1F]

2.36 mg (3.64 μmol, 0.37% yield) of N-(2-fluoro-5-{5-fluoro-3-[(2-fluoro-4-iodophenyl)amino]-2-(sulfamoylamino)phenoxy}phenyl)sulfuric diamide were isolated as a side product from the reaction mixture for example compound 14.

$^1$H-NMR (d$_6$-DMSO; 300 MHz): δ=9.35 (br. s, 1H); 8.59 (br. s, 1H); 7.64 (dd, 1H); 7.64 (br. s, 1H); 7.29-7.10 (m, 7H); 6.99 (br. s, 1H); 6.83 (ddd, 1H); 6.47 (dd, 1H); 5.99 (dd, 1H).

LC-MS: retention time: 1.24 min

MS ES$^+$: 630.3 [M+H]$^+$

Example 17

Preparation of N-(4-fluoro-2-[(2-fluoro-4-iodophenyl)amino]-6-{3-[(sulfamoylamino)methyl]phenoxy}phenyl)cyclopropanesulfonamide

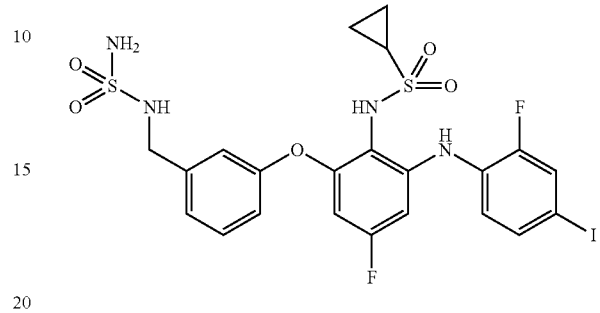

814 mg of tert-butyl [(3-{2-[(cyclopropylsulfonyl)amino]-5-fluoro-3-[(2-fluoro-4-iodophenyl)amino]phenoxy}benzyl)sulfamoyl]carbamate (Intermediate 18A; 1.08 mmol, 1 eq.) were dissolved in 30 mL DCM and 1.67 mL TFA were added. The reaction mixture was stirred at rt overnight. The reaction mixture was partitioned between saturated aq. sodium bicarbonate solution and dichloromethane. The pH was adjusted to pH=8 with aq. 2N sodium hydroxide solution. The layers were separated and the aqueouse layer reextracted twice with dichloromethane. The combined organic layers were washed once with brine, filtered and concentrated in vacuo. The crude product was purified by preparative HPLC providing 322 mg of the desired product (46% yield).

$^1$H-NMR (d$_6$-DMSO; 400 MHz): δ=9.11 (br. s, 1H); 7.64 (dd, 1H); 7.58 (br. s, 1H); 7.44 (br. d, 1H); 7.34 (dd, 1H); 7.18 (d, 1H); 7.15-7.08 (m, 3H); 6.99 (br. d, 1H); 6.62 (s, 2H); 6.55 (dd, 1H); 6.02 (dd, 1H); 4.07 (d, 2H); 2.68 (m, 1H); 0.89-0.82 (m, 4H).

LC-MS: retention time: 1.37 min

MS ES$^+$: 650.8 [M+H]$^+$

Further, the compounds of formula (I) of the present invention can be converted to any salt as described herein, by any method which is known to the person skilled in the art. Similarly, any salt of a compound of formula (I) of the present invention can be converted into the free compound, by any method which is known to the person skilled in the art.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and polyoxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al., "Compendium of Excipients for Parenteral Formulations" PDA Journal of Pharmaceutical Science a Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC-CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution: A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 minutes.

Lyophilised powder for IV administration: A sterile preparation can be prepared with (i) 100-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:

50 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Combination Therapies

The compounds of this invention can be administered as the sole pharmaceutical agent or in combination with one or more other pharmaceutical agents where the combination causes no unacceptable adverse effects. The present invention relates also to such combinations. For example, the compounds of this invention can be combined with known anti-hyper-proliferative or other indication agents, and the like, as well as with admixtures and combinations thereof. Other indication agents include, but are not limited to, anti-angiogenic agents, mitotic inhibitors, alkylating agents, anti-metabolites, DNA-intercalating antibiotics, growth factor inhibitors, cell cycle inhibitors, enzyme inhibitors, toposisomerase inhibitors, biological response modifiers, or anti-hormones.

The additional pharmaceutical agent can be aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, BCG or tice BCG, bestatin, betamethasone acetate, betamethasone sodium phosphate, bexarotene, bleomycin sulfate, broxuridine, bortezomib, busulfan, calcitonin, campath, capecitabine, carboplatin, casodex, cefesone, celmoleukin, cerubidine, chlorambucil, cisplatin, cladribine, cladribine, clodronic acid, cyclophosphamide, cytarabine, dacarbazine, dactinomycin, DaunoXome, decadron, decadron phosphate, delestrogen, denileukin diftitox, depomedrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin alfa, epogen, eptaplatin, ergamisol, estrace, estradiol, estramustine phosphate sodium, ethinyl estradiol, ethyol, etidronic acid, etopophos, etoposide, fadrozole, farston, filgrastim, finasteride, fligrastim, floxuridine, fluconazole, fludarabine, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, gleevec, gliadel, goserelin, granisetron HCl, histrelin, hycamtin, hydrocortone, eyrthro-hydroxynonyladenine, hydroxyurea, ibritumomab tiuxetan, idarubicin, ifosfamide, interferon alpha, interferon-alpha 2, interferon alfa-2A, interferon alfa-2B, interferon alfa-n1, interferon alfa-n3, interferon beta, interferon gamma-1a, interleukin-2, intron A, iressa, irinotecan, kytril, lentinan sulfate, letrozole, leucovorin, leuprolide, leuprolide acetate, levamisole, levofolinic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, Mesna, methotrexate, metvix, miltefosine, minocycline, mitomycin C, mitotane, mitoxantrone, Modrenal, Myocet, nedaplatin, neulasta, neumega, neupogen, nilutamide, nolvadex, NSC-631570, OCT-43, octreotide, ondansetron HCl, orapred, oxaliplatin, paclitaxel, pediapred, pegaspargase, Pegasys, pentostatin, picibanil, pilocarpine HCl, pirarubicin, plicamycin, porfimer sodium, prednimustine, prednisolone, prednisone, premarin, procarbazine, procrit, raltitrexed, rebif, rhenium-186 etidronate, rituximab, roferon-A, romurtide, salagen, sandostatin, sargramostim, semustine, sizofuran, sobuzoxane, solu-medrol, sparfosic acid, stem-cell therapy, streptozocin, strontium-89 chloride, synthroid, tamoxifen, tamsulosin, tasonermin, tastolactone, taxotere, teceleukin, temozolomide, teniposide, testosterone propionate, testred, thioguanine, thiotepa, thyrotropin, tiludronic acid, topotecan, toremifene, tositumomab, trastuzumab, treosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin stimalamer, zofran, ABI-007, acolbifene, actimmune, affinitak, aminopterin, arzoxifene, asoprisnil, atamestane, atrasentan, sorafenib, avastin, CCI-779, CDC-501, celebrex, cetuximab, crisnatol, cyproterone acetate, decitabine, DN101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon gamma, intron-PEG, ixabepilone, keyhole limpet hemocyanin, L-651582, lanreotide, lasofoxifene, Libra, lonafarnib, miproxifene, minodronate, MS-209, liposomal MTP-PE, MX-6, nafarelin, nemorubicin, neovastat, nolatrexed, oblimersen, onco-TCS, osidem, paclitaxel polyglutamate, pamidronate disodium, PN-401, QS-21, quazepam, R-1549, raloxifene, ranpirnase, 13-cis-retinoic acid, satraplatin, seocalcitol, T-138067, tarceva, taxoprexin, thymosin alpha 1, tiazofurine, tipifarnib, tirapazamine, TLK-286, toremifene, TransMID-107R, valspodar, vapreotide, vatalanib, verteporfin, vinflunine, Z-100, zoledronic acid or combinations thereof.

Optional anti-hyper-proliferative agents which can be added to the composition include but are not limited to compounds listed on the cancer chemotherapy drug regimens in the 11$^{th}$ Edition of the Merck Index, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use with the composition of the invention include but are not limited to those compounds acknowledged to be used in the treatment of neoplastic diseases in Goodman and Gilman's The Pharmacological Basis of Therapeutics (Ninth Edition), editor Molinoff et al., publ. by McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other anti-hyper-proliferative agents suitable for use with the composition of the invention include but are not limited to other anti-cancer agents such as epothilone and its derivatives, irinotecan, raloxifen and topotecan.

The compounds of the invention may also be administered in combination with protein therapeutics. Such protein therapeutics suitable for the treatment of cancer or other angiogenic disorders and for use with the compositions of the invention include, but are not limited to, an interferon (e.g., interferon .alpha., .beta., or .gamma.) supraagonistic monoclonal antibodies, Tuebingen, TRP-1 protein vaccine, Colostrinin, anti-FAP antibody, YH-16, gemtuzumab, infliximab, cetuximab, trastuzumab, denileukin diftitox, rituximab, thymosin alpha 1, bevacizumab, mecasermin, mecasermin rinfabate, oprelvekin, natalizumab, rhMBL, MFE-CP1+ZD-2767-P, ABT-828, ErbB2-specific immunotoxin, SGN-35, MT-103, rinfabate, AS-1402, B43-genistein, L-19 based radioimmunotherapeutics, AC-9301, NY-ESO-1 vaccine, IMC-1C11, CT-322, rhCC10, r(m)CRP, MORAb-009, aviscumine, MDX-1307, Her-2 vaccine, APC-8024, NGR-hTNF, rhH1.3, IGN-311, Endostatin, volociximab, PRO-1762, lexatumumab, SGN-40, pertuzumab, EMD-273063, L19-IL-2 fusion protein, PRX-321, CNTO-328, MDX-214, tigapotide, CAT-3888, labetuzumab, alpha-particle-emitting radioisotope-llinked lintuzumab, EM-1421, HyperAcute vaccine, tucotuzumab celmoleukin, galiximab, HPV-16-E7, Javelinprostate cancer, Javelin-melanoma, NY-ESO-1 vaccine, EGF vaccine, CYT-004-MelQbG10, WT1 peptide, oregovomab, ofatumumab, zatutumumab, cintredekin besudotox, WX-G250, Albuferon, aflibercept, denosumab, vaccine, CTP-37, efungumab, or 131I-chTNT-1/B. Monoclonal antibodies useful as the protein therapeutic include, but are not limited to, muromonab-CD3, abciximab, edrecolomab, daclizumab, gentuzumab, alemtuzumab, ibritumomab, cetuximab, bevicizumab, efalizumab, adalimumab, omalizumab, muromomab-CD3, rituximab, daclizumab, trastuzumab, palivizumab, basiliximab, and infliximab.

Generally, the use of cytotoxic and/or cytostatic agents in combination with a compound or composition of the present invention will serve to:
(1) yield better efficacy in reducing the growth of a tumor or even eliminate the tumor as compared to administration of either agent alone,
(2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

Methods of Sensitizing Cells to Radiation

In a distinct embodiment of the present invention, a compound of the present invention may be used to sensitize a cell to radiation. That is, treatment of a cell with a compound of the present invention prior to radiation treatment of the cell renders the cell more susceptible to DNA damage and cell death than the cell would be in the absence of any treatment with a compound of the invention. In one aspect, the cell is treated with at least one compound of the invention.

Thus, the present invention also provides a method of killing a cell, wherein a cell is administered one or more compounds of the invention in combination with conventional radiation therapy.

The present invention also provides a method of rendering a cell more susceptible to cell death, wherein the cell is treated one or more compounds of the invention prior to the treatment of the cell to cause or induce cell death. In one aspect, after the cell is treated with one or more compounds of the invention, the cell is treated with at least one compound, or at least one method, or a combination thereof, in order to cause DNA damage for the purpose of inhibiting the function of the normal cell or killing the cell.

In one embodiment, a cell is killed by treating the cell with at least one DNA damaging agent. That is, after treating a cell with one or more compounds of the invention to sensitize the cell to cell death, the cell is treated with at least one DNA damaging agent to kill the cell. DNA damaging agents useful in the present invention include, but are not limited to, chemotherapeutic agents (e.g., cisplatinum), ionizing radiation (X-rays, ultraviolet radiation), carcinogenic agents, and mutagenic agents.

In another embodiment, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of the invention is administered to a cell prior to the radiation or orther induction of DNA damage in the cell. In another aspect of the invention, a compound of the invention is administered to a cell concomitantly with the radiation or orther induction of DNA damage in the cell. In yet another aspect of the invention, a compound of the invention is administered to a cell immediately after radiation or orther induction of DNA damage in the cell has begun.

In another aspect, the cell is in vitro. In another embodiment, the cell is in vivo.

As mentioned supra, the compounds of the present invention have surprisingly been found to effectively inhibit allo-MEK and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by allo-MEK, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

In accordance with another aspect therefore, the present invention covers a compound of general formula (I), or a stereoisomer, a tautomer, an N-oxide, a hydrate, a solvate, or a salt thereof, particularly a pharmaceutically acceptable salt thereof, or a mixture of same, as described and defined herein, for use in the treatment or prophylaxis of a disease, as mentioned supra.

Another particular aspect of the present invention is therefore the use of a compound of general formula (I) described supra for manufacturing a pharmaceutical composition for the treatment or prophylaxis of a disease.

The diseases referred to in the two preceding paragraphs are diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The term "inappropriate" within the context of the present invention, in particular in the context of "inappropriate cellular immune responses, or inappropriate cellular inflammatory responses", as used herein, is to be understood as preferably meaning a response which is less than, or greater than normal, and which is associated with, responsible for, or results in, the pathology of said diseases.

Preferably, the use is in the treatment or prophylaxis of diseases, wherein the diseases are haemotological tumours, solid tumours and/or metastases thereof.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Kinase Disorders

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity [Aiello et al. New Engl. J. Med. 1994, 331, 1480; Peer et al. Lab. Invest. 1995, 72, 638], age-related macular degeneration [AMD; see, Lopez et al. Invest. Opththalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumor enlargement and metastasis. Moreover, the growth of new blood and lymph vessels in a tumor provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

Dose and Administration

Based upon standard laboratory techniques known to evaluate compounds useful for the treatment of hyper-proliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Preferably, the diseases of said method are haematological tumours, solid tumour and/or metastases thereof.

The compounds of the present invention can be used in particular in therapy and prevention, i.e. prophylaxis, of tumour growth and metastases, especially in solid tumours of all indications and stages with or without pre-treatment of the tumour growth.

Methods of testing for a particular pharmacological or pharmaceutical property are well known to persons skilled in the art.

The example testing experiments described herein serve to illustrate the present invention and the invention is not limited to the examples given.

Biological Evaluation

The utility of the compounds of the present invention can be illustrated, for example, by their activity in vitro in the in vitro tumor cell proliferation assay described below. The link between activity in tumor cell proliferation assays in vitro and anti-tumor activity in the clinical setting has been very well established in the art. For example, the therapeutic utility of taxol (Silvestrini et al. Stem Cells 1993, 11(6), 528-35), taxotere (Bissery et al. Anti Cancer Drugs 1995, 6(3), 339), and topoisomerase inhibitors (Edelman et al. Cancer Chemother. Pharmacol. 1996, 37(5), 385-93) were demonstrated with the use of in vitro tumor proliferation assays.

Demonstration of the activity of the compounds of the present invention may be accomplished through in vitro, ex vivo, and in vivo assays that are well known in the art. For example, to demonstrate the activity of the compounds of the present invention, the following assays may be used.

Biological Assays

In Vitro Tumor Cell Proliferation Assays:

Cell Titer Glo Proliferation Assay

The adherent tumor cell proliferation assay used to test the compounds of the present invention involves a readout called Cell Titre-Glo developed by Promega (Cunningham, B A "A Growing Issue: Cell Proliferation Assays. Modern kits ease quantification of cell growth" The Scientist 2001, 15(13), 26, and Crouch, S P et al., "The use of ATP bioluminescence as a measure of cell proliferation and cytotoxicity" *Journal of Immunological Methods* 1993, 160, 8 1-88).

Assay 1: HCT116 Cell Titer Glo (CTG) Proliferation Assay:

HCT116 cells [human colorectal cell line, expressing mutant BRAF V600E] were plated at a density of 3000 cells/well in 96 well black-clear bottom tissue culture plates (Costar 3603 black/clear bottom) in 100 µl/well DMEM medium (DMEM/Ham's F12) with 10% Fetal Bovine Serum (FBS) and stable Glutamine incubated at 37° C. Sister wells were plated in separate plate for time zero determination. All plates were incubated overnight at 37° C. Take down time zero plate: 100 µl/well CTG solution (Promega Cell Titer Glo solution) were added to time zero wells in sister plate; the plates were mixed for 2 min on orbital shaker to ensure cell lysis, incubated for 10 minutes, luminescence was read on VICTOR3

(Perkin Elmer). Twenty-four hours after cell seeding, test compounds were diluted in 50 µl medium and were added at a final concentration range from as high 10 µM to as low 300 µM depending on the activities of the tested compounds in serial dilutions at a final DMSO concentration of 0.4%. Cells were incubated for 72 hours at 37° C. after addition of the test compound. Then, using a Promega Cell Titer Glo Luminescent® assay kit, 100 µl microliter lysis buffer containing of the enzyme luciferase and its substrate, luciferin mixture, were added to each well and incubated for 10 min at room temperature in the dark to stabilize luminescence signal. The samples were read on VICTOR3 (Perkin Elmer) using Luminescence protocol. The percentage change in cell growth was calculated by normalizing the measurements to the extinctions of the zero point plate (=0%) and the extinction of the untreated (0 µM) cells (=100%). The IC50 values were determined by means of a 4-parameter fit using the company's own software.

Assay 2: A549 Cell Titer Glo (CTG) Proliferation Assay:

A549 cells [human non small cell lung cancer cell line, expressing mutant K-Ras G12S] were seeded at a density of 2000 cells/well in 96 well black-clear bottom tissue culture plates (Costar 3603 black/clear bottom) in 100 µl/well DMEM medium (DMEM/Ham's F12) with 10% Fetal Bovine Serum (FBS) and stable Glutamine incubated at 37° C. Cell Titer Glo proliferation assays for A549 cells were performed with the same protocol as described afore for HCT116 cells.

Assay 3: Colo205 Cell Titer Glo (CTG) Proliferation Assay:

Colo205 cells were plated in RPMI 1640 growth medium supplemented with 10% FBS at 3,000 cells per well in 96-well tissue culture plates. Cells were incubated overnight in a humidified incubator containing 5% $CO_2$ at 37° C. The following day, test compounds were added to wells, serially diluted in RPMI 1640 medium containing 10% FBS and 0.03% DMSO and the plates were incubated for 72 h at 37° C. Evaluation of cell density was made at different time points (0 and 72 h post-dosing) by adding to each well 150 µl of Cell Titer Glo reagent (cat# G7572, Promega, Madison Wis.) followed by incubation of the plates on a rotator for 10 min at room temperature and then reading of the luminescence on a Victor3 instrument. Data analysis was performed using Analyze5 software for $IC_{50}$ analysis.

Assay 4: A375 Cell Titer Glo (CTG) Proliferation Assay:

A375 cells [human malignant melanoma cells, ATCC # CRL-1619, expressing mutant BRAF V600E] were plated at a density of 3000 cells/well in 96 well black-clear bottom tissue culture plates (Costar 3603 black/clear bottom) in 100 µL/well DMEM medium (Biochrom; FG0435; +3.7 g/L odium bicarbonate; +4.5 g/L D-Glucose) with 10% Fetal Bovine Serum (FBS) and stable Glutaminincubated at 37° C. Plate sister wells in separate plate for time zero determination. Incubate all plates overnight 37° C. Take down time zero plate: add 67 µL/well CTG solution (Promega Cell Titer Glo solution) to time zero wells in sister plate; the plates were mixed for 2 min on orbital shaker to ensure cell lysis, incubate 10 minutes, read luminescence on VICTOR3 (Perkin Elmer). Twenty-four hours after cell seeding, test compounds diluted in 50 µL medium are added at a final concentration range from as high 10 µM to as low 300 µM depending on the activities of the tested compounds in serial dilutions at a final DMSO concentration of 0.4%. Cells were incubated for 72 hours at 37° C. after addition of the test compound. Then, using a Promega Cell Titer Glo Luminescent® assay kit, 100 microliters lysis buffer containing of the enzyme luciferase and its substrate, luciferin mixture, were added to each well and incubated for 10 min at room temperature in the dark to stabilize luminescence signal. The samples were read on VICTOR3 (Perkin Elmer) using Luminescence protocol. The percentage change in cell growth was calculated by normalizing the measurements to the extinctions of the zero point plate (=0%) and the extinction of the untreated (0 µM) cells (=100%). The IC50 values were determined by means of a 4-parameter fit using the company's own software.

Alternatively, the cell proliferation was measured by crystal violet (CV) staining:

Assay 5: A375 Crystal Violet (CV) Proliferation Assay:

Cell proliferation for A375 cells [human melanoma cell line, expressing mutant BRAF V600E] was measured by crystal violet (CV) staining: Cultivated human A375 cells were plated out in a density of 1500 cells/measurement point in 200 µl of growth medium (DMEM/HAMS F12 with 10% FBS and 2 mM Glutamine) in a 96-well multititer plate. After 24 hours, the cells from a plate (zero plate) were stained with crystal violet (see below), while the medium in the other plates was replaced by fresh culture medium (200 µl) to which the test substances had been added in various concentrations (0 µM, and in the range 0.3 nM-30 µM; the final concentration of the solvent dimethyl sulphoxide was 0.5%). The cells were incubated in the presence of the test substances for 4 days. The cell proliferation was determined by staining the cells with crystal violet: the cells were fixed by adding 20 µl/measurement point of an 11% glutaraldehyde solution at room temperature for 15 min. After the fixed cells had been washed three times with water, the plates were dried at room temperature. The cells were stained by adding 100 µl/measurement point of a 0.1% crystal violet solution (pH adjusted to pH 3 by adding acetic acid). After the stained cells had been washed three times with water, the plates were dried at room temperature. The dye was dissolved by adding 100 µl/measurement point of a 10% acetic acid solution, and the extinction was determined by photometry at a wavelength of 595 nm. The percentage change in cell growth was calculated by normalizing the measurements to the extinctions of the zero point plate (=0%) and the extinction of the untreated (0 µM) cells (=100%). The IC50 values were determined by means of a 4-parameter fit using the company's own software.

Alternatively, crystal violet (CV) staining assay may be carried out as follows:

Assay 6: Alternative Conditions for A375 Crystal Violet (CV) Proliferation Assay:

Cultivated human A375 cells were plated out in a density of 1500 cells/measurement point in 200 µl of growth medium (DMEM/HAMS F12 (Biochrom; FG4815) with 10% FBS and 2 mM Glutamine) in a 96-well multititer plate. After 24 hours, the cells from a plate (zero plate) were stained with crystal violet (see below), while the medium in the other plates was replaced by fresh culture medium (200 µl) to which the test substances had been added in various concentrations (0 µM, and in the range 0.3 nM-30 µM; the final concentration of the solvent dimethyl sulphoxide was 0.5%). The cells were incubated in the presence of the test substances for 4 days. The cell proliferation was determined by staining the cells with crystal violet: the cells were fixed by adding 20 µl/measurement point of an 11% glutaraldehyde solution at room temperature for 15 min. After the fixed cells had been washed three times with water, the plates were dried at room temperature. The cells were stained by adding 100 µl/measurement point of a 0.1% crystal violet solution (pH adjusted to pH 3 by adding acetic acid). After the stained cells had been washed three times with water, the plates were dried at room temperature. The dye was dissolved by adding 100 µl/measurement point of a 10% acetic acid solution, and the extinction was determined by photometry at a wavelength of 595 nm. The percentage change in cell growth was calculated by normalizing the measurements to the extinctions of the zero point plate (=0%) and the extinction of the untreated (0 μM) cells (=100%). The IC50 values were determined by means of a 4-parameter fit using the company's own software.

In vitro inhibition of proliferation of further cancer cell lines can be measured in analogy to the afore-described procedures. Details for exemplary further tumor cells lines are given below:

| Cells | Indication (all human) | Ras or Raf Mutation | Method | cell number per well | Medium |
|---|---|---|---|---|---|
| A-431 | epidermoid cancer | wildtype | CTG | 3000 | DMEM/HAMS F12 (Biochrom; FG4815) + 10% FBS and stable Glutamin |
| A-431 non-adherent | epidermoid cancer | wildtype | CTG | 3000 | DMEM/HAMS F12 (Biochrom; FG4815) + 10% FBS and stable Glutamin (Plates were coated with poly-2-hydroxy-ethylmethacrylate before cell seeding) |
| Colo-205 | colon carcinoma | BRAF V600E | CTG | 3000 | RPMI1640 (Biochrom; FG1215) + 10% heat inactivated FBS and stable glutamin + 1x non-essentiell amino acid + 1 mM Sodiumpyruvat + 10 mM Hepes |
| HT-29 | colon cancer | BRAF V600E | CTG | 2000 | DMEM/HAMS F12 (Biochrom; FG4815) + 10% FBS and stable Glutamin |
| Lox | melanoma | BRAF V600E | CTG | 2000 | RPMI1640 (Biochrom; FG1215) + 10% heat inactivated FBS and stable glutamin + 1x non-essentiell amino acid + 1 mM Sodiumpyruvat |
| MCF-7 | breast cancer | wildtype | CTG | 5000 | RPMI1640 (F1275; w/o phenol red) + 10% FBS + 2 mM Glutamin + 2 mU/mL Insulin + 1E-10M estradiol |

Further, the following assays may be used to assess the biological importance of the compounds of the present invention:

Assay 6
MEK Biochemical Assay: DELFIA

The DELFIA MEK kinase assay was used to monitor the activity of MEK inhibitors. The kinase reaction was carried out in a 96-well microtitration plate by firstly mixing 70 μL of kinase reaction buffer (50 mM HEPES pH 7.5, 5 mM NaF, 5 mM glycerophosphate, 1 mM sodium vanadate, 10 mM $MgCl_2$, 1 mM DTT and 1% (v/v) DMSO) with 20 nM GST-MEK, 20 nM His-Raf and 100 nM biotinylated ERK1 (final concentration). Then compounds with final concentrations of 1 μM, 0.3 μM, 0.1 μM, 0.03 μM, 0.01 μM, 0.003 μM, 0.001 μM, 0.0003 μM and 0 μM were added to generate the dose response inhibition curve. The kinase reaction was started by adding 20 μL of ATP (final concentration 100 μM). After 2 h incubation, the reaction was terminated by adding 20 μl of 0.5 M EDTA. Then 100 μL of the reaction mixture was transferred to a 96 well Streptavidin plate (cat #15120, Pierce Inc. Rockford, Ill.) and subsequently incubated for 2 h. After collecting the biotinylated substrate ERK1, the plate was washed with TBST. An antibody against phospho-p44/42 MAPK (cat#91065, Cell Signaling Technologies, Danvers, Mass.) was added and bond to the phosphorylated substrate. Thereafter, incubation with an Europium-labeled anti-mouse antibody (cat#AD0124, Wallac Inc, Turku, Finland) followed by a washing step was carried out. The Enhancement Solution was added to dissociate europium ions into solution, where they formed highly fluorescent chelates with the components of the enhancement solution. The fluorescence of each sample was proportional to kinase activity and counted on a VICTOR5 instrument (Wallac Inc.). Data analysis was performed using Analyze5 software for $IC_{50}$ analysis.

Assay 7
MEK1 Activation Kinase Assay

The kinase Cot1 activates MEK1 by phosphorylating its activation loop. The inhibitory activity of compounds of the present invention on this activation of MEK1 was quantified employing the HTRF assay described in the following paragraphs.

N-terminally His6-tagged recombinant kinase domain of the human Cot1 (amino acids 30-397, purchased from Millipore, cat. no 14-703) expressed in insect cells (SF21) and purified by Ni-NTA affinity chromatography was used as kinase. As substrate for the kinase reaction the unactive C-terminally His6-tagged GST-MEK1 fusion protein (Millipore cat. no 14-420) was used.

For the assay 50 nl of a 100 fold concentrated solution of the test compound in DMSO was pipetted into a black low volume 384 well microtiter plate (Greiner Bio-One, Frickenhausen, Germany), 3 μl of a solution of 24 nM GST-MEK1 and 166.7 μM adenosine-tri-phosphate (ATP) in assay buffer [50 mM Tris/HCl pH 7.5, 10 mM $MgCl_2$, 2 mM dithiothreitol, 0.01% (v/v) Igepal CA 630 (Sigma), 5 mM β-phospho-glycerol] were added and the mixture was incubated for 10 min at 22° C. to allow pre-binding of the test compounds to the GST-MEK1 before the start of the kinase reaction. Then the kinase reaction was started by the addition of 2 μl of a solution of Cot1 in assay buffer and the resulting mixture was incubated for a reaction time of 20 min at 22° C. The concentration of Cot1 in the assay was adjusted depending of the activity of the enzyme lot and was chosen appropriate to have the assay in the linear range, typical enzyme concentrations were in the range of about 2 ng/μl (final conc. in the 5 μl assay volume). The reaction was stopped by the addition of 5 μl of a solution of HTRF detection reagents (13 nM anti GST-XL665 [#61GSTXLB, Fa. Cis Biointernational, Marcoule, France], 1 nM Eu-cryptate labelled anti-phospho-MEK 1/2 (Ser217/221) [#61P17KAZ, Fa. Cis Biointernational],) in an aqueous EDTA-solution (100 mM EDTA, 500 mM KF, 0.2% (w/v) bovine serum albumin in 100 mM HEPES/Sodium hydroxide pH 7.5).

The resulting mixture was incubated 2 h at 22° C. to allow the binding of the phosphorylated GST-MEK1 to the anti-GST-XL665 and the Eu-cryptate labelled anti-phospho-MEK 1/2 antibody. Subsequently the amount of Ser217/Ser221-phosphorylated substrate was evaluated by measurement of the resonance energy transfer from the Eu-Cryptate-labelled anti-phospho-MEK antibody to the anti-GST-XL665. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Normally test compound were tested on the same microtiter plate at 10 different concentrations in the range of 20 μM to 1 nM (20 μM, 6.7 μM, 2.2 μM, 0.74 μM, 0.25 μM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values were calculated by a 4 parameter fit using an inhouse software.

Assay 8
Phospho-ERK Mechanistic Assay

A375 and Colo205 cells were plated in RPMI 1640 growth medium supplemented with 10% FBS at 25,000 cells per well in 96-well tissue culture plates. Cells were incubated overnight in a humidified incubator containing 5% $CO_2$ at 37° C. The following day, to prepare the assay plates, anti-rabbit Meso-Scale Discovery (MSD) plates (cat# L41 RA-1, Meso-Scale Discovery, Gaithersburg, Md.) were blocked with 100 μl of 5% MSD blocking buffer for 1 h at room temperature, after which they were washed three times with 200 μl of TBST buffer. The phospho-ERK rabbit polyclonal antibody (cat#9101, Cell Signaling Technologies, Danvers, Mass.) diluted at 1:200 into 2.5% of MSD Blocker A-TBST was added (25 μl) to each well and the plate was then incubated 1 h at room temperature with shaking. The plates were then washed once with phosphate buffered saline (PBS) and ready to receive the cell lysates. While the preparation of the assay plates was ongoing, test compounds were added to the wells of cell-containing plates from the previous day, serially diluted in RPMI 1640 medium containing 10% FBS, 0.1% bovine serum albumin (BSA) and 0.03% DMSO and the plates were incubated for 1.5 h at 37° C. After this incubation, the compound-treated plates were washed three times with PBS, lysed in 30 μl of Bio-Rad lysis buffer (cat #98601, Bio-Rad Laboratories, Hercules, Calif.) and then left shaking on ice for 30 min. The lysates were then loaded on the phospho-ERK coated MSD plates and the plates Incubated overnight at 4° C. The following day, the plates were washed three times with TBST and 25 μl of 1:3000 diluted total ERK monoclonal antibody (Cat#610123, BD Biosciences, San Diego, Calif.) was added to the plates that were then incubated 1 h at room temperature with shaking. After the incubation the plates were washed three times with TBST as described earlier and 25 μl of MSD sulfo-tag anti-mouse antibody (cat #R32AC-5) diluted 1:1000 were added into each well. The plates were Incubated 1 h at room temperature with shaking, then washed four times with TBST. Just prior to reading the plates, 150 μl of MSD Read buffer T was added and the plates were read immediately on the MSD instrument. Data analysis was performed using Analyze5 software for $IC_{50}$ analysis.

Assay 9
Alternative Conditions for Mechanistic pERK Assay

For the measurement of ERK1/2 phosphorylation in tumor cell lines a singleplex Mesoscale Discovery (MSD) assay is used. This assay is built up like a sandwich immunoassay. Cell lysates generated from different tumor cell lines treated with serially diluted MEK inhibitor compounds were loaded on the MSD plates. Phosphorylated ERK1/2 present in the samples binds to the capture antibody immobilized on the working electrode surface. The sandwich is completed by binding of a detection antibody to the immobilzed phospho-ERK1/2. This detection antibody is labeled with an electrochemiluminescent compound. Applying voltage to the plate electrodes causes the labels, bound to the electrode surface via the antibody-phospho ERK1/2 sandwich complex, to emit light. The measurement of the emitted light allows a quantitative determination of the amount of phosphorylated ERK1/2 present in the sample. In detail, a linear range for the measurement of phosphoERK signals must be determined for every cell line used in the assay by titrating different cell numbers. For the final assay, the previously determined cell number is seeded in 96 well plates. 24 h after seeding, cells were treated for 1.5 h with serially diluted allosteric MEK inhibitor compounds before the cells were lysed and lysates were transferred in the MSD assay plate. The manufacturer's protocol was changed in that the binding step of the phosphorylated ERK to the capture antibody was performed over night at 4° C. instead of 3 h at room temperature, leading to a better signal strength.

A375 or Colo205 cells were plated in 50 μL DMEM growth medium (Biochrom FG 0435) supplemented with 10% FBS (Biochrom #S0410) (A375), respectively in RPMI growth medium (Biochrom FG1215) supplemented with 10% FBS (Biochrom #S0410), 10 mM HEPES (Biochrom L1613), 4.5 g/L Glucose and 1 mM sodiumpyruvat (Biochrom L0473) (Colo-205) at 45000 cells per well in 96-well tissue culture plates. Cells were incubated overnight in a humidified incubator containing 5% $CO_2$ at 37° C.

The Phospho-ERK by Mesoscale Discovery (MSD) (# K111DWD) assay was performed according to the manufacturer's recommendations. In brief the protocol was:

The day after cell seeding, to prepare the assay plates, MSD were blocked with 150 μl of MSD blocking buffer for 1 h at room temperature, after which they were washed four times with 150 μl of Tris Wash buffer. While the preparation of the assay plates was ongoing, test compounds were added to the wells of cell-containing plates from the previous day, serially diluted in respective growth medium containing 10% FBS and 0.1% DMSO and the plates were incubated for 1.5-2 h at 37° C. After this incubation the medium was aspirated, cells were lysed in 50 μl lysis buffer and then left shaking for 30 min at 4° C. 25 μL of the lysates were then loaded on the blocked MSD plates and the plates Incubated overnight at 4° C. The following day, the plates were washed four times with Tris wash buffer and 25 μl detection antibody solution was added to the plates that were then incubated 1 h at room temperature with shaking. After the incubation the plates were washed four times with Tris wash buffer 150 μl of MSD Read buffer T was added and the plates were read immediately on the MSD instrument. Data analysis was performed using an in-house software for IC50 analysis.

Assay 10

In Vivo Efficacy Studies: Staged Human Xenograft Models

The in vivo anti-tumor activity of lead compounds was assessed in mice using xenograft models of human BRAF mutant melanoma and colon carcinomas. The Female athymic NCR nude mice were implanted subcutaneously with either a human melanoma (LOX), or a human colon (Colo205) carcinoma lines acquired from American Type Culture Collection (ATCC, Maryland). Treatment was initiated when tumors reached approximately 100 mg in size. Compounds were administered orally and freshly prepared in PEG/water (80%/20% respectively). The general health of mice was monitored and mortality was recorded daily. Tumor dimensions and body weights were recorded twice a week starting with the first day of treatment. Animals were euthanized according to Bayer IACUC guidelines. Treatments producing greater than 20% lethality and/or 20% net body weight loss were considered 'toxic'.

Tumor growth was measured with electronic calipers three times a week and tumor weight (mg) calculated according to the following formula: [length (mm)×width (mm)$^2$]/2. Anti-tumor efficacy was determined as a function of tumor growth inhibition (% TGI). TGI is calculated on days of measurement using the following formula: (100−mean tumor value of treated (T)/mean tumor of control value (C)×100)=% T/C. The control used in the calculations is either the "untreated control" or "vehicle", whichever provides the most conservative representation of the data. A compound demonstrating a TGI of greater than or equal to 50% is considered active. Statistical significance is determined using either a one-tailed or two-tailed Student's T-Test. The compounds that were tested showed significant dose-dependent tumor growth inhibition in both LOX and Colo205 models.

Compounds of the invention were tested for activity using one or more of the assay procedures presented above.

The following Table shows IC50 values obtained in the above-mentioned Assays 1, 2 and 5, for compounds of the present invention, in comparison to IC50 values for a compound of prior art document WO 2008/138639, as follows:

| Example No | Structure | A375 Proliferation Assay (CV) [Assay 5] IC$_{50}$ [M] | HCT116 Proliferation Assay (CTG) [Assay 1] IC$_{50}$ [M] | A549 Proliferation Assay (CTG) [Assay 2] IC$_{50}$ [M] |
|---|---|---|---|---|
| Reference example cmpd 6.7 from WO 2008138639 | 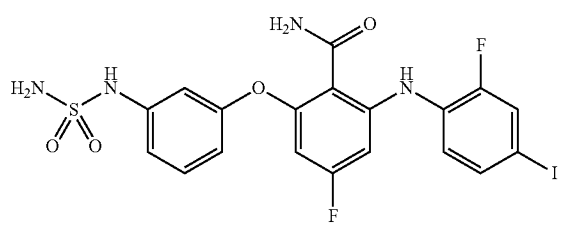 [SMILES: NC(=O)c1c(Nc2ccc(I)cc2F)cc(F)cc1Oc1cccc(NS(N)(=O)=O)c1] | 4.53E−9 | 2.08E−7 | 3.19E−7 |
| 1 | 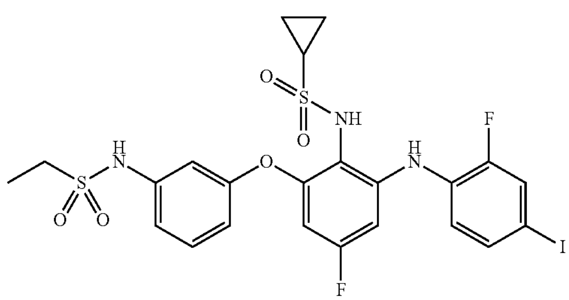 [SMILES: CCS(=O)(=O)Nc1cccc(Oc2cc(F)cc(Nc3ccc(I)cc3F)c2NS(=O)(=O)C2CC2)c1] | 3.51E−10 | 2.65E−8 | 1.81E−8 |
| 6 | 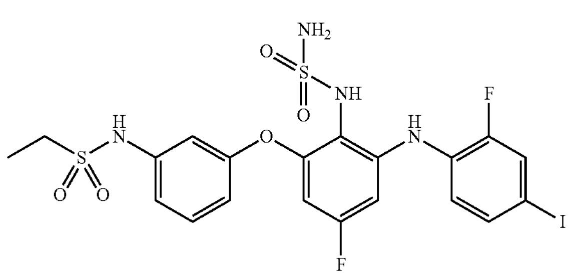 [SMILES: CCS(=O)(=O)Nc1cccc(Oc2cc(F)cc(Nc3ccc(I)cc3F)c2NS(N)(=O)=O)c1] | 2.44E−9 | 1.0E−7 | 6.89E−8 |

-continued

| Example No | Structure | A375 Proliferation Assay (CV) [Assay 5] IC$_{50}$ [M] | HCT116 Proliferation Assay (CTG) [Assay 1] IC$_{50}$ [M] | A549 Proliferation Assay (CTG) [Assay 2] IC$_{50}$ [M] |
|---|---|---|---|---|
| 7 | 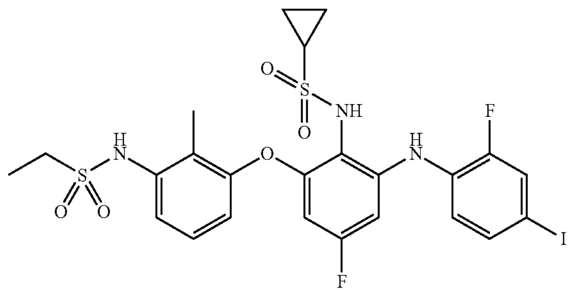 [SMILES: CCS(=O)(=O)Nc1cccc(Oc2cc(F)cc(Nc3ccc(I)cc3F)c2NS(=O)(=O)C2CC2)c1C] | 1.71E−10 | 3.0E−9 | |
| 8 | 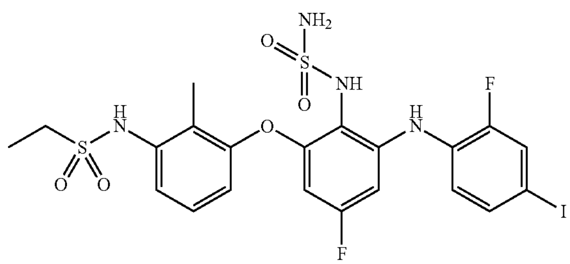 [SMILES: CCS(=O)(=O)Nc1cccc(Oc2cc(F)cc(Nc3ccc(I)cc3F)c2NS(N)(=O)=O)c1C] | 6.8E−10 | 1.0E−8 | 4.78E−9 |
| 9 | 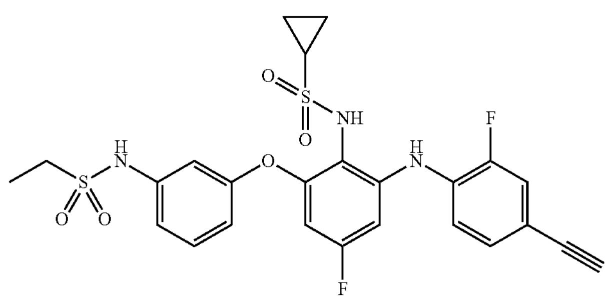 [SMILES: C#Cc1ccc(Nc2cc(F)cc(Oc3cccc(NS(=O)(=O)CC)c3)c2NS(=O)(=O)C2CC2)c(F)c1] | 2.39E−9 | 5.96E−8 | 1.37E−7 |
| 3 | 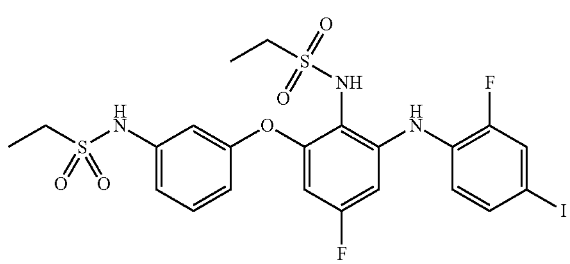 [SMILES: CCS(=O)(=O)Nc1cccc(Oc2cc(F)cc(Nc3ccc(I)cc3F)c2NS(=O)(=O)CC)c1] | 1.56E−9 | 3.17E−8 | 7.36E−8 |
| 4 | 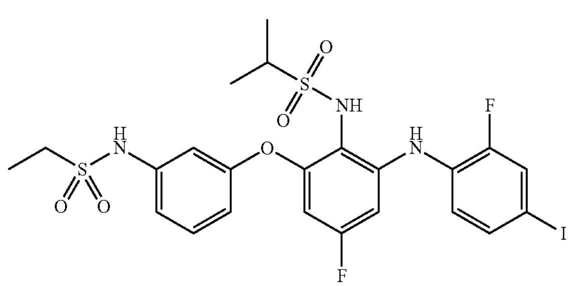 [SMILES: CCS(=O)(=O)Nc1cccc(Oc2cc(F)cc(Nc3ccc(I)cc3F)c2NS(=O)(=O)C(C)C)c1] | 1.56E−8 | 5.37E−8 | 9.25E−8 |

-continued

| Example No | Structure | A375 Proliferation Assay (CV) [Assay 5] IC$_{50}$ [M] | HCT116 Proliferation Assay (CTG) [Assay 1] IC$_{50}$ [M] | A549 Proliferation Assay (CTG) [Assay 2] IC$_{50}$ [M] |
|---|---|---|---|---|
| 2 | 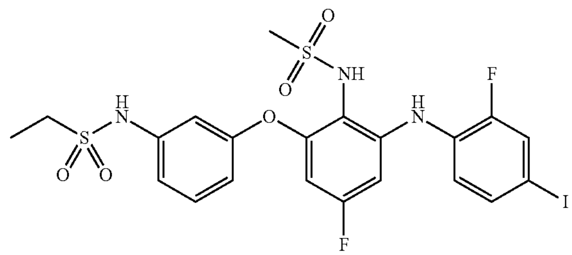 [SMILES: CCS(=O)(=O)Nc1cccc(Oc2cc(F)cc(Nc3ccc(I)cc3F)c2NS(C)(=O)=O)c1] | 8.99E−10 | 2.83E−8 | 3.94E−8 |
| 10 | 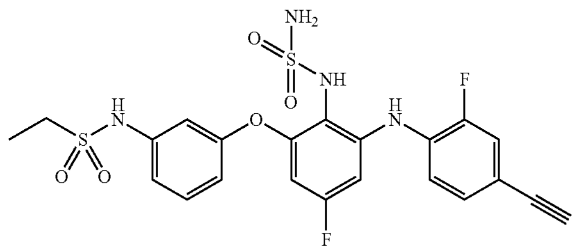 [SMILES: C#Cc1ccc(Nc2cc(F)cc(Oc3cccc(NS(=O)(=O)CC)c3)c2NS(N)(=O)=O)c(F)c1] | 7.93E−9 | 7.0E−8 | 8.67E−8 |
| 11 | 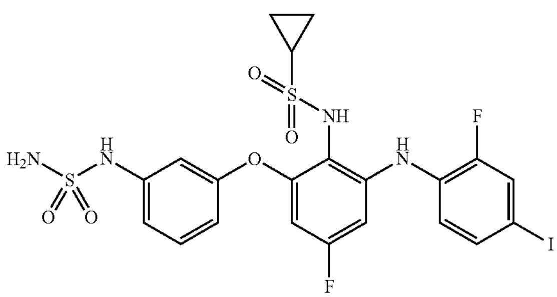 [SMILES: NS(=O)(=O)Nc1cccc(Oc2cc(F)cc(Nc3ccc(I)cc3F)c2NS(=O)(=O)C2CC2)c1] | | 7.04E−9 | 6.65E−9 |
| 12 | 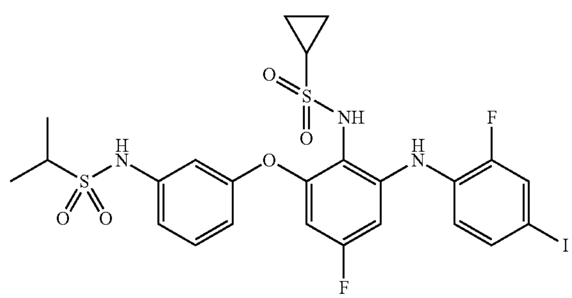 [SMILES: CC(C)S(=O)(=O)Nc1cccc(Oc2cc(F)cc(Nc3ccc(I)cc3F)c2NS(=O)(=O)C2CC2)c1] | 7.29E−10 | 3.2E−8 | 3.61E−8 |
| 14 | 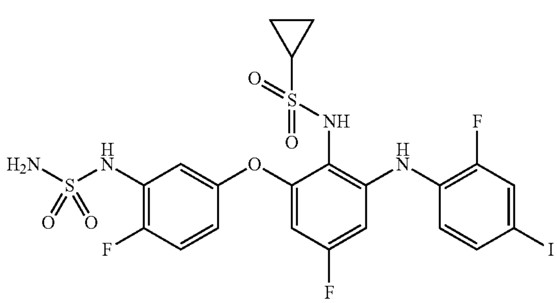 [SMILES: NS(=O)(=O)Nc1cc(Oc2cc(F)cc(Nc3ccc(I)cc3F)c2NS(=O)(=O)C2CC2)ccc1F] | 1.86E−8 | | |

It is believed that one skilled in the art, using the preceding information and information available in the art, can utilize the present invention to its fullest extent. Those skilled in the art will recognize that the invention may be practiced with variations on the disclosed structures, materials, compositions and methods without departing from the spirit or scope of the invention as it is set forth herein and such variations are regarded as within the ambit of the invention. The compounds described in the examples are intended to be representative of the invention, and it will be understood that the scope of the invention is not limited by the scope of the examples. The topic headings set forth above are meant as guidance where certain information can be found in the application, but are not intended to be the only source in the application where information on such topics can be found. All publications and patents cited above are incorporated herein by reference.

REFERENCES

[1] American Cancer Society, Cancer Facts and Figures 2005.
[2] Sausville E A, El Sayed Y, Monga M, Kim G. Signal Transduction Directed Cancer Treatments. Annu Rev Pharmacol Toxicol 2002; 43: 199-231.
[3] O'Dwyer M E, Mauro M J, Druker B J. STI571 as a targeted therapy for CML. Cancer Invest 2003; 21: 429-438.
[4] de Jong F A, Verweij J. Rote of imatinib mesylate (Gleevec/Glivec) in gastrointestinal stromal tumors. Expert Rev Anticancer Ther 2003; 3: 757-766.
[4] Becker J. Signal transduction inhibitors—a work in progress. Nature Biotech 2004; 22: 15-18.
[5] Cobb M H. MAP kinase pathways. Prog Biophys Mot Biol 1999; 71: 479-500.
[6] Lewis T S, Shapiro P S, Ahn N G. Signal transduction through MAP kinase cascades. Adv Cancer Res 1998; 74: 49-139.
is [7] English J M, Cobb M H. Pharmacological inhibitors of MAPK pathways. Trends Pharmacol Sci 2002; 23: 40-45.
[8] Duesbery N S, Webb C P, Vande Woude G F. MEK wars, a new front in the battle against cancer. Nat Med 1999; 5: 736-737.
[9] Sebolt-Leopold J S. Development of anticancer drugs targeting the MAP kinase pathway. Oncogene 2000; 19: 6594-6599.
[10] Milella M, Precupanu C M, Gregorj C, Ricciardi M R, Petrucci M T, Kornblau S M, Tafuri A, Andreeff M. Beyond single pathway inhibition: MEK inhibitors as a platform for the development of pharmacological combinations with synergistic anti-leukemic effects. Curr Pharm Des. 2005; 11(21):2779-95.
[11] Hancock C N, Macias A T, Mackerell A D Jr, Shapiro P. Mitogen activated protein (MAP) kinases: development of ATP and non-ATP dependent inhibitors. Med. Chem. 2006 March; 2(2):213-22.
[12] Deramaudt T, Rustgi A K. Mutant KRAS in the initiation of pancreatic cancer. Biochim Biophys Acta. 2005; 1756 (2):97-101.
[13] Libra M, Malaponte G, Navolanic P M, Gangemi P, Bevelacqua V, Proietti L, Bruni B, Stivala F, Mazzarino M C, Travali S, McCubrey J A. Analysis of BRAF mutation in primary and metastatic melanoma. Cell Cycle. 2005 October; 4(10):1382-4.
[14] Herrera R, Sebolt-Leopold J S. Unraveling the complexities of the Raf/MAP kinase pathway for pharmacological intervention. Trends Mol Med 2002; 8: S27-S31.
[15] Alessi D R, Cuenda A, Cohen P, Dudley D T, Saltiel A R. PD 098059 is a specific inhibitor of the activation of mitogenactivated protein kinase kinase in vitro and in vivo. J Biol Chem 1995; 270: 27489-27494.
[16] Favata M F, Horiuchi K Y, Manos E J, Daulerio A J, Stradley D A, Feeser W S, et al. Identification of a novel inhibitor of mitogenactivated protein kinase kinase. J Biol Chem 1998; 273: 18623-18632.
[17] Allen L F, Sebolt-Leopold J, Meyer M B. CI-1040 (PD184352), a targeted signal transduction inhibitor of MEK (MAPKK). Semin Oncol 2003; 30: 105-116.
[18] Sebolt-Leopold J S, Dudley D T, Herrera R, Van Becelaere K, Wiland A, Gowan R C, et al. Blockade of the MAP kinase pathway suppresses growth of colon tumors in vivo. Nat Med 1999; 5: 810-816
[19] Waterhouse D, Rinehart J, Adjei A, Hecht J, Natale R, LoRusso P, et al. A phase 2 study of an oral MEK inhibitor, CI-1040, in patients with advanced non small-cell lung, breast, colon, or pancreatic cancer. Proc Am Soc Clin Oncol 2003; 22: 204a (abstr).

The invention claimed is:
1. A compound of general formula (I):

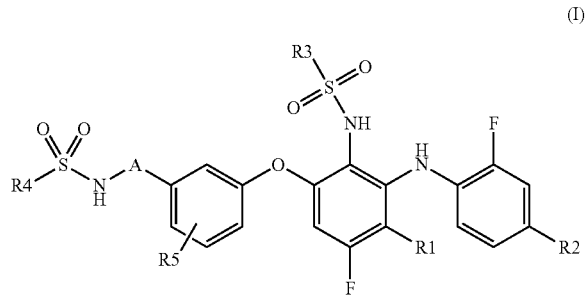

in which:
R1 is a hydrogen atom or a fluorine atom;
R2 is a halogen atom or a $C_2$-alkynyl or cyano group;
R3 is an —$NH_2$, —$NH(C_1$-$C_6$-alkyl), —$N(C_1$-$C_6$-alkyl)$_2$, —$C_1$-$C_6$-alkyl, or —$C_3$-$C_6$-cycloalkyl group;
R4 is an —$NH_2$, —$NH(C_1$-$C_6$-alkyl), —$N(C_1$-$C_6$-alkyl)$_2$, —$C_1$-$C_6$-alkyl, or —$C_3$-$C_6$-cycloalkyl group;
R5 is a hydrogen atom, a halogen atom, or a —$C_1$-$C_6$-alkyl or —O—$C_1$-$C_6$-alkyl group;
A is —$(CH_2)_n$—, in which n=0, or 1;
or a tautomer, stereoisomer, N-oxide, salt, hydrate, or solvate thereof.

2. The compound according to claim 1, wherein:
R1 is a hydrogen atom or a fluorine atom;
R2 is a fluorine atom or a $C_2$-alkynyl or cyano group;
R3 is an —$NH_2$, —$NH(C_1$-$C_6$-alkyl), —$N(C_1$-$C_6$-alkyl)$_2$, —$C_1$-$C_6$-alkyl, or —$C_3$-$C_6$-cycloalkyl group;
R4 is an —$NH_2$, —$NH(C_1$-$C_6$-alkyl), —$N(C_1$-$C_6$-alkyl)$_2$, —$C_1$-$C_6$-alkyl, or —$C_3$-$C_6$-cycloalkyl group;
R5 is a hydrogen atom, a fluorine atom or a methyl group;
A is —$(CH_2)_n$—, in which n=0, or 1;
or a tautomer, stereoisomer, N-oxide, salt, hydrate, or solvate thereof.

3. The compound according to claim 1, wherein:
R1 is a hydrogen atom or a fluorine atom;
R2 is a fluorine atom or a $C_2$-alkynyl or cyano group;
R3 is an —$NH_2$, —$NH(C_1$-$C_6$-alkyl), —$N(C_1$-$C_6$-alkyl)$_2$, —$C_1$-$C_6$-alkyl, or —$C_3$-$C_6$-cycloalkyl group;
R4 is an —$NH_2$, methyl, ethyl, n-propyl, iso-propyl, cyclopropyl or cyclobutyl group;
R5 is a hydrogen atom, a fluorine atom or a methyl group;
A is —$(CH_2)_n$—, in which n=0, or 1;
or a tautomer, stereoisomer, N-oxide, salt, hydrate, or solvate thereof.

4. The compound according to claim 1, wherein:
R1 is a hydrogen atom or a fluorine atom;
R2 is a fluorine atom or a $C_2$-alkynyl or cyano group;

R3 is an —NH$_2$, methyl, ethyl, n-propyl, iso-propyl, cyclopropyl or cyclobutyl group;

R4 is an —NH$_2$, methyl, ethyl, n-propyl, iso-propyl, cyclopropyl or cyclobutyl group;

R5 is a hydrogen atom, a fluorine atom or a methyl group;

A is —(CH$_2$)$_n$—, in which n=0, or 1;

or a tautomer, stereoisomer, N-oxide, salt, hydrate, or solvate thereof.

5. The compound according to claim 1, which is selected from the group consisting of:

N-(2-{3-[(ethylsulfonyl)amino]phenoxy}-4-fluoro-6-[(2-fluoro-4-iodophenyl)amino]phenyl)cyclopropanesulfonamide;

N-(3-{5-fluoro-3-[(2-fluoro-4-iodophenyl)amino]-2-[(methylsulfonyl)-amino]phenoxy}-phenyl)ethane-sulfonamide;

N-(3-{2-[(ethylsulfonyl)amino]-5-fluoro-3-[(2-fluoro-4-iodophenyl)amino]-phenoxy}phenyl)-ethanesulfonamide;

N-(2-{3-[(ethylsulfonyl)amino]phenoxy}-4-fluoro-6-[(2-fluoro-4-iodophenyl)amino]-phenyl)propane-2-sulfonamide;

N-(2-{3-[(ethylsulfonyl)amino]phenoxy}-4-fluoro-6-[(2-fluoro-4-iodophenyl)amino]-phenyl)cyclobutane-sulfonamide;

N-(3-{5-fluoro-3-[(2-fluoro-4-iodophenyl)amino]-2-(sulfamoylamino)phenoxy}phenyl)ethanesulfonamide;

N-(2-{3-[(ethylsulfonyl)amino]-2-methylphenoxy}-4-fluoro-6-[(2-fluoro-4-iodophenyl)amino]phenyl)cyclopropanesulfonamide;

N-(3-{5-fluoro-3-[(2-fluoro-4-iodophenyl)amino]-2-(sulfamoylamino)phenoxy}-2-methylphenyl)ethanesulfonamide;

N-(2-{3-[(ethylsulfonyl)amino]phenoxy}-6-[(4-ethynyl-2-fluorophenyl)amino]-4-fluorophenyl)cyclopropanesulfonamide;

N-(3-{3-[(4-ethynyl-2-fluorophenyl)amino]-5-fluoro-2-(sulfamoylamino)phenoxy}phenyl)ethanesulfonamide [Formic Acid salt];

N-{4-fluoro-2-[(2-fluoro-4-iodophenyl)amino]-6-[3-(sulfamoylamino)phenoxy]phenyl}cyclopropanesulfonamide;

N-(4-fluoro-2-[(2-fluoro-4-iodophenyl)amino]-6-{3-[(isopropylsulfonyl)amino]phenoxy}phenyl)cyclopropanesulfonamide;

N-(4-fluoro-2-[(2-fluoro-4-iodophenyl)amino]-6-{3-[(methylsulfonyl)amino]phenoxy}phenyl)cyclopropanesulfonamide;

N-{4-fluoro-2-[(2-fluoro-4-iodophenyl)amino]-6-[4-fluoro-3-(sulfamoylamino)phenoxy]phenyl}cyclopropanesulfonamide;

N-(5{2-[(cyclopropylsulfonyl)amino]-5-fluoro-3-[(2-fluoro-4-iodophenyl)amino]phenoxy}-2-fluorophenyl)cyclopropanesulfonamide;

N-(2-fluoro-5-{5-fluoro-3-[(2-fluoro-4-iodophenyl)amino]-2-(sulfamoylamino)phenoxy}phenyl)sulfuric diamide; and N-(4-fluoro-2-[(2-fluoro-4-iodophenyl)amino]-6-{3-[(sulfamoylamino)methyl]phenoxy}phenyl)cyclopropanesulfonamide.

6. A method of preparing a compound of general formula (I) according to claim 1, said method comprising the step of allowing an intermediate compound of general formula (4):

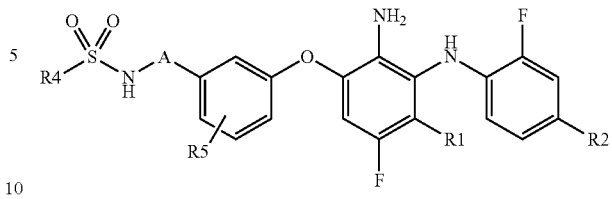

in which R1, R2, R4, R5 and A are as defined in claim 1, to react with a sulphonyl chloride of general formula E:

in which R3 is as defined in claim 1, thereby giving a compound of general formula I:

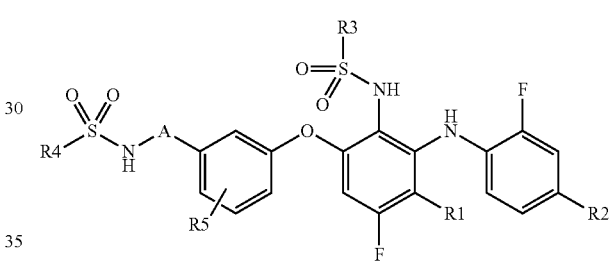

in which R1, R2, R3, R4, R5 and A are as defined in claim 1.

7. A method of preparing a compound of general formula (I) according to claim 1, said method comprising the step of allowing an intermediate compound of general formula (8):

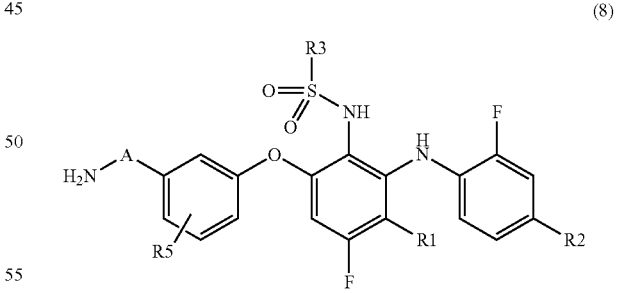

in which R1, R2, R3, R5 and A are as defined in claim 1, to react with a sulphonyl chloride of general formula D:

in which R4 is as defined in claim 1, thereby giving a compound of general formula I:

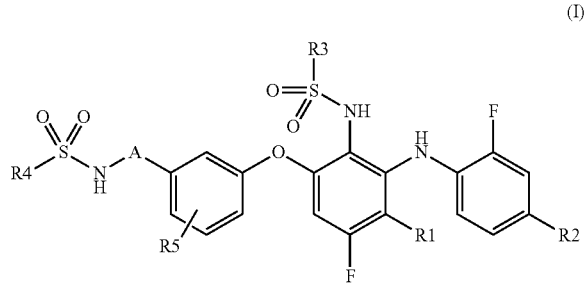

(I)

in which R1, R2, R3, R4, R5 and A are as defined in claim 1.

8. A method of preparing a compound of general formula (Ic), said method comprising the step of allowing an intermediate compound of general formula (12):

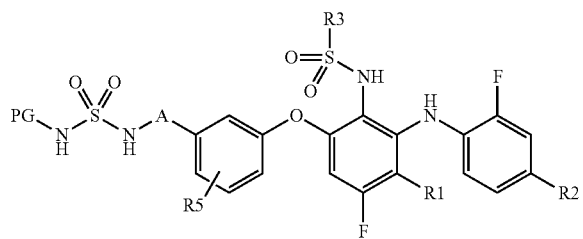

(12)

in which $R^1$, $R^2$, $R^3$, $R^5$, and A are as defined in claim 1, and PG represents an acid labile protecting group,
to react with an acid, thereby giving a compound of formula (Ic):

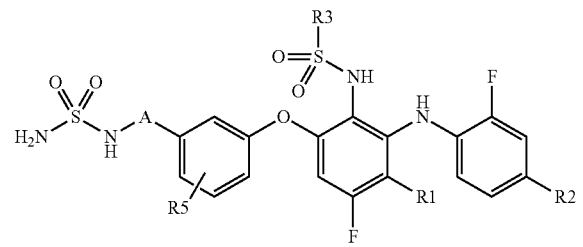

(Ic)

in which $R^1$, $R^2$, $R^3$, $R^5$ and A are as defined in claim 1.

9. A pharmaceutical composition comprising a compound of general formula (I), or a stereoisomer, a tautomer, an N-oxide, a hydrate, a solvate, or a pharmaceutically acceptable salt thereof, or a mixture of same, according to claim 1, and a pharmaceutically acceptable diluent or carrier.

10. A pharmaceutical combination comprising:
one or more compounds of general formula (I), or a stereoisomer, a tautomer, an N-oxide, a hydrate, a solvate, or a pharmaceutically acceptable salt thereof, or a mixture of same, according to claim 1;

and one or more agents selected from: a taxane; an epothilone; Mitoxantrone; Prednisolone; Dexamethasone; Estramustin; Vinblastin; Vincristin; Doxorubicin; Adriamycin; Idarubicin; Daunorubicin; Bleomycin; Etoposide; Cyclophosphamide; Ifosfamide; Procarbazine; Melphalan; 5-Fluorouracil; Capecitabine; Fludarabine; Cytarabine; Ara-C; 2-Chloro-2'-deoxyadenosine; Thioguanine; an anti-androgen; Bortezomib; a platinum derivative; Chlorambucil; Methotrexate; and Rituximab.

11. A method for the treatment of uncontrolled cell growth, proliferation and/or survival, an inappropriate cellular immune response, or an inappropriate cellular inflammatory response, wherein the uncontrolled cell growth, proliferation and/or survival, inappropriate cellular immune response, or inappropriate cellular inflammatory response is mediated by the mitogen-activated protein kinase (MEK-ERK) pathway, comprising administering to a human in need thereof a therapeutically acceptable amount of a compound of general formula (I), or a stereoisomer, a tautomer, an N-oxide, a hydrate, a solvate, or a pharmaceutically acceptable salt thereof, or a mixture of same, according to claim 1.

12. The method according to claim 11, wherein the uncontrolled cell growth, proliferation and/or survival, inappropriate cellular immune response, or inappropriate cellular inflammatory response is a haemotological tumour, a solid tumour and/or metastases thereof.

13. The method according to claim 12, wherein the haemotological tumour, solid tumour and/or metastases thereof is selected from leukaemias and myelodysplastic syndrome, malignant lymphomas, head and neck tumours, brain tumours and brain metastases, tumours of the thorax, non-small cell and small cell lung tumours, gastrointestinal tumours, endocrine tumours, mammary and other gynaecological tumours, urological tumours, renal, bladder and prostate tumours, skin tumours, and sarcomas, and/or metastases thereof.

* * * * *